(12) United States Patent
Gefen et al.

(10) Patent No.: US 9,474,902 B2
(45) Date of Patent: Oct. 25, 2016

(54) WEARABLE APPARATUS FOR DELIVERY OF POWER TO A RETINAL PROSTHESIS

(71) Applicant: NANO RETINA LTD., Herzliya (IL)

(72) Inventors: Ra'anan Gefen, Re'ut (IL); Leonid Yanovitz, Rishon Lezion (IL); Kobi Kamintz, Tel Aviv (IL); Shai Eisenberg, Givat Ellea (IL)

(73) Assignee: NANO RETINA LTD., Herzliya Pituach (IL)

( * ) Notice: Subject to any disclaimer, the term of this patent is extended or adjusted under 35 U.S.C. 154(b) by 181 days.

(21) Appl. No.: 14/145,470

(22) Filed: Dec. 31, 2013

(65) Prior Publication Data

US 2015/0182748 A1    Jul. 2, 2015

(51) Int. Cl.
| | |
|---|---|
| *A61N 1/36* | (2006.01) |
| *A61N 1/378* | (2006.01) |
| *F21V 8/00* | (2006.01) |
| *G02B 6/26* | (2006.01) |
| *G02C 7/08* | (2006.01) |

(Continued)

(52) U.S. Cl.
CPC ......... *A61N 1/36046* (2013.01); *A61N 1/3787* (2013.01); *G02B 6/0016* (2013.01); *G02B 6/0055* (2013.01); *G02B 6/26* (2013.01); *G02B 27/017* (2013.01); *G02B 27/0172* (2013.01); *G02C 7/086* (2013.01); *G02C 11/10* (2013.01); *A61B 2560/0219* (2013.01); *A61F 2250/0001* (2013.01); *G02B 27/0093* (2013.01); *G02B 2027/0114* (2013.01); *G02B 2027/0138* (2013.01); *G02B 2027/0178* (2013.01); *G02B 2027/0187* (2013.01)

(58) Field of Classification Search
CPC .................................................. A61N 1/36046
See application file for complete search history.

(56) References Cited

U.S. PATENT DOCUMENTS

| | | | |
|---|---|---|---|
| 1,662,446 A | 3/1928 | Wappler | |
| 2,721,316 A | 10/1955 | Shaw | |

(Continued)

FOREIGN PATENT DOCUMENTS

| | | |
|---|---|---|
| CA | 2235216 | 4/1997 |
| CN | 1875895 | 12/2006 |

(Continued)

OTHER PUBLICATIONS

ISR and written opinion, dated Feb. 27, 2014, which issued in PCT/IB2013/060270.

(Continued)

*Primary Examiner* — Carl H Layno
*Assistant Examiner* — Jennifer Ghand
(74) *Attorney, Agent, or Firm* — Sughrue Mion, PLLC

(57) ABSTRACT

Apparatus is provided including an extraocular device, which includes an eyeglasses frame, which is placed in front of an eye of a subject, and a power source coupled to the eyeglasses frame and configured to emit a beam of light that is outside of 380-750 nm. A light-guiding element is coupled to the eyeglasses frame and at least one optical coupling-in element and at least one optical coupling-out element are optically coupled to the light-guiding element. The coupling-in element is positioned such that the beam of light is directed into the light-guiding element via the coupling-in element, and the coupling-in and coupling-out elements are positioned such that the beam diverges from a focal point located within 3 mm of the coupling-out element. Other applications are also described.

12 Claims, 8 Drawing Sheets

(51) Int. Cl.
  *G02C 11/00* (2006.01)
  *G02B 27/01* (2006.01)
  *G02B 27/00* (2006.01)

(56) References Cited

U.S. PATENT DOCUMENTS

| | | | |
|---|---|---|---|
| 2,760,483 A | 8/1956 | Tassicker | |
| 4,197,850 A | 4/1980 | Schulman et al. | |
| 4,262,294 A | 4/1981 | Hara et al. | |
| 4,272,910 A | 6/1981 | Danz | |
| 4,324,252 A | 4/1982 | Rossing et al. | |
| 4,551,149 A | 11/1985 | Sciarra | |
| 4,601,545 A | 7/1986 | Kern | |
| 4,628,933 A | 12/1986 | Michelson | |
| 4,664,117 A | 5/1987 | Beck | |
| 4,786,818 A | 11/1988 | Mead et al. | |
| 4,837,049 A | 6/1989 | Byers et al. | |
| 4,903,702 A | 2/1990 | Putz | |
| 4,914,738 A | 4/1990 | Oda et al. | |
| 4,969,468 A | 11/1990 | Byers et al. | |
| 5,016,633 A | 5/1991 | Chow | |
| 5,024,223 A | 6/1991 | Chow | |
| 5,081,378 A | 1/1992 | Watanabe | |
| 5,108,427 A | 4/1992 | Majercik et al. | |
| 5,109,844 A | 5/1992 | de Juan, Jr. et al. | |
| 5,133,356 A | 7/1992 | Bryan et al. | |
| 5,147,284 A | 9/1992 | Fedorov et al. | |
| 5,159,927 A | 11/1992 | Schmid | |
| 5,215,088 A | 6/1993 | Normann et al. | |
| 5,313,642 A | 5/1994 | Seigel | |
| 5,314,458 A | 5/1994 | Najafi et al. | |
| 5,397,350 A | 3/1995 | Chow et al. | |
| 5,411,540 A | 5/1995 | Edell et al. | |
| 5,476,494 A | 12/1995 | Edell et al. | |
| 5,526,423 A | 6/1996 | Ohuchi et al. | |
| 5,556,423 A | 9/1996 | Chow et al. | |
| 5,575,813 A | 11/1996 | Edell et al. | |
| 5,597,381 A | 1/1997 | Rizzo, III | |
| 5,608,204 A | 3/1997 | Hofflinger et al. | |
| 5,674,263 A | 10/1997 | Yamamoto et al. | |
| 5,735,882 A | 4/1998 | Rottenberg et al. | |
| 5,769,875 A | 6/1998 | Peckham et al. | |
| 5,800,478 A | 9/1998 | Chen et al. | |
| 5,800,533 A | 9/1998 | Eggleston et al. | |
| 5,800,535 A | 9/1998 | Howard, III | |
| 5,805,267 A | 9/1998 | Goldman et al. | |
| 5,835,250 A | 11/1998 | Kanesaka | |
| 5,836,996 A | 11/1998 | Doorish | |
| 5,837,995 A | 11/1998 | Chow et al. | |
| 5,850,514 A | 12/1998 | Gonda et al. | |
| 5,865,839 A | 2/1999 | Doorish | |
| 5,873,901 A | 2/1999 | Wu et al. | |
| 5,895,415 A | 4/1999 | Chow et al. | |
| 5,935,155 A | 8/1999 | Humayun et al. | |
| 5,944,747 A | 8/1999 | Greenberg et al. | |
| 5,949,064 A | 9/1999 | Chow et al. | |
| 6,020,593 A | 2/2000 | Chow et al. | |
| 6,032,062 A | 2/2000 | Nisch | |
| 6,035,236 A | 3/2000 | Jarding et al. | |
| 6,043,437 A | 3/2000 | Schulman et al. | |
| 6,069,365 A | 5/2000 | Chow et al. | |
| 6,075,251 A | 6/2000 | Chow et al. | |
| 6,201,234 B1 | 3/2001 | Chow et al. | |
| 6,230,057 B1 | 5/2001 | Chow et al. | |
| 6,235,046 B1 | 5/2001 | Gerdt et al. | |
| 6,259,937 B1 | 7/2001 | Schulman et al. | |
| 6,287,372 B1 | 9/2001 | Briand et al. | |
| 6,298,270 B1 | 10/2001 | Nisch et al. | |
| 6,319,273 B1 | 11/2001 | Chen et al. | |
| 6,324,429 B1 | 11/2001 | Shire et al. | |
| 6,347,250 B1 | 2/2002 | Nisch et al. | |
| 6,368,349 B1 | 4/2002 | Wyatt et al. | |
| 6,389,317 B1 | 5/2002 | Chow et al. | |
| 6,400,989 B1 | 6/2002 | Eckmiller | |
| 6,427,087 B1 | 7/2002 | Chow et al. | |
| 6,442,431 B1 | 8/2002 | Veraart et al. | |
| 6,458,157 B1 | 10/2002 | Suaning | |
| 6,472,122 B1 | 10/2002 | Schulman et al. | |
| 6,473,365 B2 | 10/2002 | Joh et al. | |
| 6,498,043 B1 | 12/2002 | Schulman et al. | |
| 6,507,758 B1 | 1/2003 | Greenberg et al. | |
| 6,533,798 B2 | 3/2003 | Greenberg et al. | |
| 6,574,022 B2 | 6/2003 | Chow et al. | |
| 6,611,716 B2 | 8/2003 | Chow et al. | |
| 6,647,297 B2 | 11/2003 | Scribner | |
| 6,658,299 B1 | 12/2003 | Dobelle | |
| 6,677,225 B1 | 1/2004 | Ellis et al. | |
| 6,678,458 B2 | 1/2004 | Ellis et al. | |
| 6,683,645 B1 | 1/2004 | Collins et al. | |
| 6,738,672 B2 | 5/2004 | Schulman et al. | |
| 6,755,530 B1 | 6/2004 | Loftus et al. | |
| 6,758,823 B2 | 7/2004 | Pasquale et al. | |
| 6,761,724 B1 | 7/2004 | Zrenner et al. | |
| 6,762,116 B1 | 7/2004 | Skidmore | |
| 6,770,521 B2 | 8/2004 | Visokay et al. | |
| 6,785,303 B1 | 8/2004 | Holzwarth et al. | |
| 6,792,314 B2 | 9/2004 | Byers et al. | |
| 6,804,560 B2 | 10/2004 | Nisch et al. | |
| 6,821,154 B1 | 11/2004 | Canfield et al. | |
| 6,844,023 B2 | 1/2005 | Schulman et al. | |
| 6,847,847 B2 | 1/2005 | Nisch et al. | |
| 6,888,571 B1 | 5/2005 | Koshizuka et al. | |
| 6,904,239 B2 | 6/2005 | Chow et al. | |
| 6,908,470 B2 | 6/2005 | Stieglitz et al. | |
| 6,923,669 B1 | 8/2005 | Tsui et al. | |
| 6,935,897 B2 | 8/2005 | Canfield et al. | |
| 6,949,763 B2 | 9/2005 | Ovadia et al. | |
| 6,961,619 B2 | 11/2005 | Casey | |
| 6,970,745 B2 | 11/2005 | Scribner | |
| 6,974,533 B2 | 12/2005 | Zhou | |
| 6,976,998 B2 | 12/2005 | Rizzo et al. | |
| 6,990,377 B2 | 1/2006 | Gliner et al. | |
| 7,001,608 B2 | 2/2006 | Fishman et al. | |
| 7,003,354 B2 | 2/2006 | Chow et al. | |
| 7,006,873 B2 | 2/2006 | Chow et al. | |
| 7,025,619 B2 | 4/2006 | Tsui et al. | |
| 7,027,874 B1 | 4/2006 | Sawan et al. | |
| 7,031,776 B2 | 4/2006 | Chow et al. | |
| 7,035,692 B1 | 4/2006 | Maghribi et al. | |
| 7,037,943 B2 | 5/2006 | Peyman | |
| 7,047,080 B2 | 5/2006 | Palanker et al. | |
| 7,058,455 B2 | 6/2006 | Huie, Jr. et al. | |
| 7,071,546 B2 | 7/2006 | Fey et al. | |
| 7,079,881 B2 | 7/2006 | Schulman et al. | |
| 7,081,630 B2 | 7/2006 | Saini et al. | |
| 7,096,568 B1 | 8/2006 | Nilsen et al. | |
| 7,103,416 B2 | 9/2006 | Ok et al. | |
| 7,107,097 B2 | 9/2006 | Stern et al. | |
| 7,127,286 B2 | 10/2006 | Mech et al. | |
| 7,127,301 B1 | 10/2006 | Okandan et al. | |
| 7,130,693 B1 | 10/2006 | Montalbo | |
| 7,133,724 B2 | 11/2006 | Greenberg et al. | |
| 7,139,612 B2 | 11/2006 | Chow et al. | |
| 7,147,865 B2 | 12/2006 | Fishman et al. | |
| 7,149,586 B2 | 12/2006 | Greenberg et al. | |
| 7,158,834 B2 | 1/2007 | Paul, Jr. | |
| 7,158,836 B2 | 1/2007 | Suzuki | |
| 7,160,672 B2 | 1/2007 | Schulman et al. | |
| 7,162,308 B2 | 1/2007 | O'Brien et al. | |
| 7,177,697 B2 | 2/2007 | Eckmiller et al. | |
| 7,190,051 B2 | 3/2007 | Mech et al. | |
| 7,191,010 B2 | 3/2007 | Ohta et al. | |
| 7,224,300 B2 | 5/2007 | Dai et al. | |
| 7,224,301 B2 | 5/2007 | Dai et al. | |
| 7,235,350 B2 | 6/2007 | Schulman et al. | |
| 7,242,597 B2 | 7/2007 | Shodo | |
| 7,244,027 B2 | 7/2007 | Sumiya | |
| 7,248,928 B2 | 7/2007 | Yagi | |
| 7,251,528 B2 | 7/2007 | Harold | |
| 7,255,871 B2 | 8/2007 | Huie, Jr. et al. | |
| 7,257,446 B2 | 8/2007 | Greenberg et al. | |
| 7,263,403 B2 | 8/2007 | Greenberg et al. | |
| 7,271,525 B2 | 9/2007 | Byers et al. | |
| 7,272,447 B2 | 9/2007 | Stett et al. | |

(56) References Cited

U.S. PATENT DOCUMENTS

| | | |
|---|---|---|
| 7,291,540 B2 | 11/2007 | Mech et al. |
| 7,295,872 B2 | 11/2007 | Kelly et al. |
| 7,302,598 B2 | 11/2007 | Suzuki et al. |
| 7,314,474 B1 | 1/2008 | Greenberg et al. |
| 7,321,796 B2 | 1/2008 | Fink et al. |
| 7,342,427 B1 | 3/2008 | Fensore et al. |
| 7,377,646 B2 | 5/2008 | Suzuki |
| 7,379,000 B2 | 5/2008 | Dal et al. |
| 7,388,288 B2 | 6/2008 | Solzbacher et al. |
| 7,400,021 B2 | 7/2008 | Wu et al. |
| 7,447,547 B2 | 11/2008 | Palanker |
| 7,447,548 B2 | 11/2008 | Eckmiller |
| 7,480,988 B2 | 1/2009 | Ok et al. |
| 7,481,912 B2 | 1/2009 | Stelzle et al. |
| 7,482,957 B2 | 1/2009 | Dal et al. |
| 7,483,751 B2 | 1/2009 | Greenberg et al. |
| 7,493,169 B2 | 2/2009 | Greenberg et al. |
| 7,499,754 B2 | 3/2009 | Greenberg et al. |
| 7,539,544 B2 | 5/2009 | Greenberg et al. |
| 7,542,209 B2 | 6/2009 | McGuire, Jr. |
| 7,555,328 B2 | 6/2009 | Schulman et al. |
| 7,556,621 B2 | 7/2009 | Palanker et al. |
| 7,565,202 B2 | 7/2009 | Greenberg et al. |
| 7,565,203 B2 | 7/2009 | Greenberg et al. |
| 7,571,004 B2 | 8/2009 | Roy et al. |
| 7,571,011 B2 | 8/2009 | Zhou et al. |
| 7,574,263 B2 | 8/2009 | Greenberg et al. |
| 7,595,933 B2 | 9/2009 | Tang |
| 7,610,098 B2 | 10/2009 | McLean |
| 7,622,702 B2 | 11/2009 | Wu et al. |
| 7,630,771 B2 | 12/2009 | Cauller |
| 7,631,424 B2 | 12/2009 | Greenberg et al. |
| 7,638,032 B2 | 12/2009 | Zhou et al. |
| 7,643,214 B2 | 1/2010 | Amitai |
| 7,666,523 B2 | 2/2010 | Zhou |
| 7,676,274 B2 | 3/2010 | Hung et al. |
| 7,691,252 B2 | 4/2010 | Zhou et al. |
| 7,706,887 B2 | 4/2010 | Tai et al. |
| 7,706,893 B2 | 4/2010 | Hung et al. |
| 7,709,961 B2 | 5/2010 | Greenberg et al. |
| 7,725,191 B2 | 5/2010 | Greenberg et al. |
| 7,734,352 B2 | 6/2010 | Greenberg et al. |
| 7,738,962 B2 | 6/2010 | Greenberg et al. |
| 7,749,608 B2 | 7/2010 | Laude et al. |
| 7,750,076 B2 | 7/2010 | Laude et al. |
| 7,751,896 B2 | 7/2010 | Graf et al. |
| 7,765,009 B2 | 7/2010 | Greenberg et al. |
| 7,766,903 B2 | 8/2010 | Blumenkranz et al. |
| 7,776,197 B2 | 8/2010 | Zhou |
| 7,831,309 B1 | 11/2010 | Humayun et al. |
| 7,834,767 B2 | 11/2010 | Shodo |
| 7,835,798 B2 | 11/2010 | Greenberg et al. |
| 7,840,273 B2 | 11/2010 | Schmid |
| 7,846,285 B2 | 12/2010 | Zhou et al. |
| 7,853,330 B2 | 12/2010 | Bradley et al. |
| 7,871,707 B2 | 1/2011 | Laude et al. |
| 7,877,866 B1 | 2/2011 | Greenberg et al. |
| 7,881,799 B2 | 2/2011 | Greenberg et al. |
| 7,887,681 B2 | 2/2011 | Zhou |
| 7,894,909 B2 | 2/2011 | Greenberg et al. |
| 7,894,911 B2 | 2/2011 | Greenberg et al. |
| 7,904,148 B2 | 3/2011 | Greenberg et al. |
| 7,908,011 B2 | 3/2011 | McMahon et al. |
| 7,912,556 B2 | 3/2011 | Greenberg et al. |
| 7,914,842 B1 | 3/2011 | Greenberg et al. |
| 7,937,153 B2 | 5/2011 | Zhou et al. |
| 7,957,811 B2 | 6/2011 | Caspi et al. |
| 7,962,221 B2 | 6/2011 | Greenberg et al. |
| 7,979,134 B2 | 7/2011 | Chow et al. |
| 7,989,080 B2 | 8/2011 | Greenberg et al. |
| 8,000,804 B1 | 8/2011 | Wessendorf et al. |
| 8,010,202 B2 | 8/2011 | Shah et al. |
| 8,010,206 B2 | 8/2011 | Dai et al. |
| 8,014,868 B2 | 9/2011 | Greenberg et al. |
| 8,014,869 B2 | 9/2011 | Greenberg et al. |
| 8,014,878 B2 | 9/2011 | Greenberg et al. |
| 8,024,022 B2 | 9/2011 | Schulman et al. |
| 8,034,229 B2 | 10/2011 | Zhou et al. |
| 8,046,078 B2 | 10/2011 | Greenberg et al. |
| 8,060,211 B2 | 11/2011 | Greenberg et al. |
| 8,060,216 B2 | 11/2011 | Greenberg et al. |
| 8,068,913 B2 | 11/2011 | Greenberg et al. |
| 8,078,284 B2 | 12/2011 | Greenberg et al. |
| 8,090,447 B2 | 1/2012 | Tano et al. |
| 8,090,448 B2 | 1/2012 | Greenberg et al. |
| 8,103,352 B2 | 1/2012 | Fried et al. |
| 8,121,697 B2 | 2/2012 | Greenberg et al. |
| 8,131,375 B2 | 3/2012 | Greenberg et al. |
| 8,131,378 B2 | 3/2012 | Greenberg et al. |
| 8,145,322 B1 | 3/2012 | Yao et al. |
| 8,150,526 B2 | 4/2012 | Gross et al. |
| 8,150,534 B2 | 4/2012 | Greenberg et al. |
| 8,160,713 B2 | 4/2012 | Greenberg et al. |
| 8,165,680 B2 | 4/2012 | Greenberg et al. |
| 8,170,676 B2 | 5/2012 | Greenberg et al. |
| 8,170,682 B2 | 5/2012 | Greenberg et al. |
| 8,180,453 B2 | 5/2012 | Greenberg et al. |
| 8,180,454 B2 | 5/2012 | Greenberg et al. |
| 8,180,460 B2 | 5/2012 | Nevsmith et al. |
| 8,190,267 B2 | 5/2012 | Greenberg et al. |
| 8,195,266 B2 | 6/2012 | Whalen, III et al. |
| 8,197,539 B2 | 6/2012 | Nasiatka et al. |
| 8,220,966 B2 | 7/2012 | Mukawa |
| 8,239,034 B2 | 8/2012 | Greenberg et al. |
| 8,244,362 B2 | 8/2012 | Yonezawa |
| 8,294,994 B1 | 10/2012 | Kelly |
| 8,359,083 B2 | 1/2013 | Clark et al. |
| 8,428,740 B2 | 4/2013 | Gefen et al. |
| 8,446,675 B1 | 5/2013 | Wang et al. |
| 8,477,425 B2 | 7/2013 | Border et al. |
| 2001/0011844 A1 | 8/2001 | Ernst et al. |
| 2002/0091421 A1 | 7/2002 | Greenberg et al. |
| 2003/0023297 A1 | 1/2003 | Byers et al. |
| 2003/0032946 A1 | 2/2003 | Fishman et al. |
| 2003/0086064 A1 | 5/2003 | Sutter |
| 2003/0100823 A1 | 5/2003 | Kipke et al. |
| 2003/0132946 A1 | 7/2003 | Gold |
| 2003/0181957 A1 | 9/2003 | Greenberg et al. |
| 2003/0208248 A1 | 11/2003 | Carter et al. |
| 2004/0054407 A1 | 3/2004 | Tashiro et al. |
| 2004/0078064 A1 | 4/2004 | Suzuki |
| 2004/0080026 A1 | 4/2004 | Minamio et al. |
| 2004/0082981 A1 | 4/2004 | Chow et al. |
| 2004/0088026 A1 | 5/2004 | Chow et al. |
| 2004/0098067 A1 | 5/2004 | Ohta et al. |
| 2004/0181265 A1 | 9/2004 | Palanker et al. |
| 2004/0189940 A1 | 9/2004 | Kutschbach et al. |
| 2005/0013005 A1 | 1/2005 | Rogers |
| 2005/0015120 A1 | 1/2005 | Seibel et al. |
| 2005/0119605 A1 | 6/2005 | Sohn |
| 2005/0146954 A1 | 7/2005 | Win et al. |
| 2005/0168569 A1 | 8/2005 | Igarashi et al. |
| 2006/0106432 A1 | 5/2006 | Sawan et al. |
| 2006/0111757 A9 | 5/2006 | Greenberg et al. |
| 2006/0136018 A1 | 6/2006 | Lack et al. |
| 2006/0184245 A1 | 8/2006 | Graf et al. |
| 2006/0256989 A1 | 11/2006 | Olsen et al. |
| 2006/0282128 A1 | 12/2006 | Tai et al. |
| 2006/0287688 A1 | 12/2006 | Yonezawa |
| 2007/0005116 A1 | 1/2007 | Lo |
| 2007/0047091 A1 | 3/2007 | Spitzer et al. |
| 2007/0064310 A1 | 3/2007 | Mukawa et al. |
| 2007/0123766 A1 | 5/2007 | Whalen et al. |
| 2007/0142877 A1 | 6/2007 | McLean |
| 2007/0142878 A1 | 6/2007 | Krulevitch et al. |
| 2007/0191909 A1 | 8/2007 | Ameri et al. |
| 2008/0114230 A1 | 5/2008 | Addis |
| 2008/0234791 A1 | 9/2008 | Arle et al. |
| 2008/0247722 A1 | 10/2008 | Van Gorkom et al. |
| 2008/0262571 A1 | 10/2008 | Greenberg et al. |
| 2008/0288036 A1 | 11/2008 | Greenberg et al. |
| 2008/0288067 A1 | 11/2008 | Flood |
| 2008/0294224 A1 | 11/2008 | Greenberg et al. |
| 2009/0002034 A1 | 1/2009 | Westendorp et al. |

(56) References Cited

U.S. PATENT DOCUMENTS

| | | |
|---|---|---|
| 2009/0005835 A1 | 1/2009 | Greenberg et al. |
| 2009/0024182 A1 | 1/2009 | Zhang et al. |
| 2009/0040461 A1 | 2/2009 | Efron et al. |
| 2009/0118805 A1 | 5/2009 | Greenberg et al. |
| 2009/0147331 A1 | 6/2009 | Ashkenazi |
| 2009/0192571 A1 | 7/2009 | Stett et al. |
| 2009/0204207 A1 | 8/2009 | Blum et al. |
| 2009/0204212 A1 | 8/2009 | Greenberg et al. |
| 2009/0216295 A1 | 8/2009 | Zrenner et al. |
| 2009/0228069 A1 | 9/2009 | Dai et al. |
| 2009/0287275 A1 | 11/2009 | Suaning et al. |
| 2009/0326623 A1 | 12/2009 | Greenberg et al. |
| 2010/0087895 A1 | 4/2010 | Zhou et al. |
| 2010/0174224 A1 | 7/2010 | Sohn |
| 2010/0204754 A1 | 8/2010 | Gross et al. |
| 2010/0249877 A1 | 9/2010 | Naughton |
| 2010/0249878 A1 | 9/2010 | McMahon et al. |
| 2010/0331682 A1 | 12/2010 | Stein et al. |
| 2011/0054583 A1 | 3/2011 | Litt et al. |
| 2011/0106229 A1 | 5/2011 | Ortmann |
| 2011/0172736 A1 | 7/2011 | Gefen et al. |
| 2011/0254661 A1 | 10/2011 | Fawcett et al. |
| 2012/0013843 A1 | 1/2012 | Jannard |
| 2012/0035725 A1 | 2/2012 | Gefen et al. |
| 2012/0035726 A1 | 2/2012 | Gross et al. |
| 2012/0041514 A1 | 2/2012 | Gross et al. |
| 2012/0069448 A1 | 3/2012 | Sugihara |
| 2012/0194781 A1 | 8/2012 | Agurok |
| 2012/0194871 A1 | 8/2012 | Murata |
| 2012/0209350 A1 | 8/2012 | Taylor et al. |
| 2012/0215291 A1 | 8/2012 | Pugh et al. |
| 2012/0221103 A1 | 8/2012 | Liran et al. |
| 2012/0259410 A1 | 10/2012 | Gefen et al. |
| 2012/0268080 A1 | 10/2012 | Jeon et al. |
| 2012/0283800 A1 | 11/2012 | Perryman et al. |
| 2013/0044042 A1 | 2/2013 | Olsson et al. |
| 2013/0126713 A1 | 5/2013 | Haas et al. |
| 2013/0322462 A1 | 12/2013 | Poulsen |
| 2014/0031931 A1 | 1/2014 | Liran et al. |
| 2014/0047713 A1 | 2/2014 | Singh et al. |

FOREIGN PATENT DOCUMENTS

| | | |
|---|---|---|
| DE | 10315397 | 10/2004 |
| JP | 2000-350742 | 12/2000 |
| JP | 2003-528702 | 9/2003 |
| WO | WO0191854 | 12/2001 |
| WO | WO03032946 | 4/2003 |
| WO | WO2007006376 | 1/2007 |
| WO | WO2007009539 | 1/2007 |
| WO | WO 2007/076347 | 5/2007 |
| WO | WO2007095395 | 8/2007 |
| WO | WO2010035173 | 4/2010 |
| WO | WO2010089739 | 8/2010 |
| WO | WO2011086545 | 7/2011 |
| WO | WO 2011/163262 A2 | 12/2011 |
| WO | 2012/017426 | 2/2012 |
| WO | 2012/114327 | 8/2012 |
| WO | WO 2012/114327 | 8/2012 |
| WO | WO/2012/153325 | 11/2012 |

OTHER PUBLICATIONS

Examination Report, dated Apr. 16, 2014, which issued during prosecution of EP11732733.8.

Official Action, dated Nov. 27, 2013, which issued during prosecution of JP 2011-548843.

Examination Report, dated Feb. 26, 2014, which issued during prosecution of EP10738277.2.

Extended European Search Report, dated Nov. 19, 2013, which issued during the prosecution of European Patent Application No. 11814197.7.

J.F. Rizzo, "Methods and Perceptual Thresholds for Short-Term Electrical Stimulation of Human Retina with Microelectrode Arrays", Investigative Ophthalmology and Visual Science, vol. 44, No. 12, (Dec. 1, 2003) pp. 5355-5361.

Official Action dated Oct. 22, 2013, which issued during the prosecution of Applicant's U.S. Appl. No. 13/148,461.

Normann et al., "High-resolution spatio-temporal mapping of visual pathways using multi-electrode arrays," Vision Research 41 (2001) 1261-1275.

Notice of Allowance issued in U.S. Appl. No. 13/437,310, dated Jan. 28, 2014.

Partial ISR dated Jun. 16, 2014 for PCT/IB2014/059672.

Stanford University, Office of Technology Licensing, Ref. 11-165—Eyeglasses mounted display (http://techfinder.stanford.edu/technology_detail.php?ID=28805).

Delbruck et al.: "Analog VLSI Adaptive, Logarithmic, Wide-Dynamic-Range Photoreceptor," 1994 International Symposium on Circuits and Systems (London, 1994), p. 339-342.

Grill W., at al., Implanted Neural Interfaces: Biochallenges and Engineered Solutions, Annu. Rev. Biomed. Eng. 2009, 11:1.

Jourdain R P., at al., "Fabrication of piezoelectric thick-film bimorph micro-actuators from bulk ceramics using batch-scale methods" Multi-Material Micro Manufacture, S. Dimov and W. Menz (Eds.) 2008 Cardiff University, Cardiff, UK., Whittles Publishing Ltd.

Kim B., "Through-Silicon-Via Copper Deposition for Vertical Chip Integration" Master. Res, Soc. Symp. Proc. vol. 970, 2007 Material Research Society.

Lianga C, at al., "Surface modification of cp-Ti using femtosecond laser micromachining and the deposition of Ca/P layer" Materials Letters vol. 62, Issue 23, Aug. 31, 2008, pp. 3783-3786—an abstract.

David C Ng, et al., "Pulse frequency modulation based CMOS image sensor for subretinal stimulation" IEEE Transactions on Circuits and Systems—II: Express Briefs, vol. 53, No. 6, Jun. 2006.

News Release—Sony develops back-illuminated CMOS image sensor, realizing high picture quality, nearly twofold sensitivity (*1) and low noise, Jun. 2008 http://www.sony.net/SonyInfo/News/Press/200806/08-069E/index.html.

Puech M., et al., "Fabrication of 3D packaging TSV using DRIE" ALCATEL Micro Machining Systems, www.adixen.com, Mar. 2007.

Seo J M., et al., "Biocompatibility of polyimide microelectrode array for retinal stimulation," Materials Science and Engineering: C, vol. 24, No. 1, Jan. 5, 2004, pp. 185-189(5).

Sorkin R., et al., "Process entanglement as a neuronal anchorage mechanism to rough surfaces," Nanotechnology 20 (2009) 015101 (8pp).

Starzyk JA, et al., "A DC-DC charge pump design based on voltage doublers" IEEE Transaction on Circuits and Systems—I: Fundamental theory and applications, vol. 48, No. 3 Mar. 2001.

Stein DJ, et al., "High voltage with Si series photovoltaics" Proceedings of SPE, the International Society for Optical Engineering 2006, vol. 6287, pp. 62870D.1-62870D, (an abstract).

Swain P K., et al., "Back-Illuminated Image Sensors Come to the Forefront. Novel materials and fabrication methods increase quality and lower cost of sensors for machine vision and industrial imaging." Photonics Spectra Aug. 2008.

Vorobyeva A Y. at al., "Metallic light absorbers produced by femtosecond laser pulses," Advances in Mechanical Engineering vol. 2010, Article ID 452749, 4 pages doi:10.1155/2010/452749, Hindawi Publishing Corporation.

Vorobyeva A Y. et al., "Femtosecond laser structuring of titanium implants," Applied Surface Science vol. 253, Issue 17, Jun. 30, 2007, pp. 7272-7280—an abstract.

Wallman L., et al., "The geometric design of micromachined silicon sieve electrodes influences functional nerve regeneration," Biomaterials May 2001:22(10):1 187-93, (an abstract).

(56) References Cited

OTHER PUBLICATIONS

Walter P., et al., "Cortical Activation via an implanted wireless retinal prosthesis," Investigative Ophthalmology and Visual Science. 2005;46:1780-1785.
Wu J T. and Chang K L., "MOS charge pumps for low-voltage operation" IEEE Journal of Solid-State Circuits, vol. 33 No. 4 Apr. 1998.
Zrenner E., 2002. "Will retinal implants restore vision?" Science 295(5557), pp. 1022-1025.
Office Action dated Aug. 24, 2011 issued during the prosecution of related U.S. Appl. No. 12/368,150.
International Preliminary Report on Patentability and Written Opinion dated Aug. 9, 2011, issued in related International Application No. PCT/IL2010/000097.
International Search Report dated Aug. 17, 2010, issued in related International Application No. PCT/IL2010/000097.
International Search Report and Written Opinion dated Aug. 12, 2011, issued in related International Application No. PCT/IL2011/000022.
International Search Report and Written Opinion dated Dec. 12, 2011 issued in related International Application No. PCT/IL2011/00609.
An Office Action dated Aug. 28, 2012, which issued during the prosecution of U.S. Appl. No. 12/852,218.
An Office Action dated Sep. 28, 2012, which issued during the prosecution of U.S. Appl. No. 13/103,264.
An International Preliminary Report on Patentability dated Jul. 17, 2012, which issued during the prosecution of Applicant's PCT/IL2011/000022.
A Supplementary European Search Report dated Aug. 10, 2012, which issued during the prosecution of Applicant's European Application No. 10 73 8277.
Palanker D. et al., "Design of a high-resolution optoelectric retinal prosthesis". Journal of Neural Engineering, Institute of physics publishing, Bristol, GB. vol. 2, No. 1, Mar. 1, 2005 (Mar. 1, 2005), pp. S105-S120, XP002427333, ISSN: 17412552, DOI: 10.1088/1741-2560/2/1/012.
Cortical Visual Neuro-Prosthesis for the Blind: Retina-Like Software/Hardware Preprocessor, F.J. Pelayol, A. Martinezl, S. Romerol, Ch.A. Morillasl, E. Rosl , E. Fernandez2 1Dept. of Computer Architecture and Technology, University of Granada, Spain 2Dept. of Histology and Institute of Bioengineering, University Miguel Hernandez, Alicante, Spain Neural Engineering, 2003. Conference Proceedings. First International IEEE EMBS Conference.
"Single-Chip CMOS Image Sensors for a Retina Implant System", Markus Schwarz, Ralf Hauschild, Bedrich J. Hosticka, Senior Member, IEEE, Jurgen Huppertz, Student Member, IEEE, Thorsten Kneip, Member, IEEE, Stephan Kolnsberg, Lutz Ewe, and Hoc Khiem Trieu, 2000.
An International Search Report dated Aug. 12, 2011, which issued during the prosecution of Applicant s PCT/IL2011/000022.
An International Search Report and a Written Opinion both dated Sep. 17, 2012, which issued during the prosecution of Applicant's PCT/IL12/00057.

Schwarz et al. "Hardware Architecture of a Neural Net Based Retina Implant for Patients Suffering from Retinitis Pigmentosa," Fraunhofer Institute of Microelectronic Circuits and Systems, pp. 653-658 (1996).
Ganesan et al. "Diamond Penetrating Electrode Array for Epi-Retinal Prosthesis," 32nd Annual International Conference of the IEEE EMBS, pp. 6757-6760 (2010).
Finn, et al. "An Amphibian Model for Developing and Evaluating Retinal Protheses," 18th Annual International Conference of the IEEE Engineering in Medicine and Biology Society, pp. 1540-1541 (1996).
Shawn Kelly, "A System for Electrical Retinal Stimulation for Human Trials," Massachusetts Institute of Technology, pp. 1-45 (1998).
Andreou et al. "Analog Integrated Circuits and Signal Processing," An International Journal, vol. 9, No. 2, pp. 141-1 66 (1996).
Office Action for U.S. Appl. No. 13/034,516 dated Dec. 14, 2012.
Office Action for U.S. Appl. No. 12/687,509 dated Dec. 7, 2012.
Office Action for U.S. Appl. No. 13/148,461 dated Mar. 13, 2013.
Office Action for U.S. Appl. No. 12/687,509 dated Jun. 6, 2013.
International Search Report and Written Opinion for International Application No. PCT/IL2012/000186 dated Sep. 4, 2012.
Humayun et al. "Visual perception in a blind subject with a chronic microelectronic retinal prosthesis," Vision Research, vol. 43, pp. 2573-2581 (2003).
Tran et al. "A Fully Flexible Stimulator using 65 nm CMOS Process for 1024-electrode Epi-retinal Prosthesis," 31st Annual International Conference of the IEEE EMBS, pp. 1643-1646 (2009).
Office Action issued in U.S. Appl. No. 13/437,310, dated Aug. 12, 2013.
An interview summary in U.S. Appl. No. 13/437,310 dated Nov. 14, 2013 in connection with the Office Action issued on Aug. 12, 2013.
European Search Report for European Application No. EP11732733 dated Jul. 16, 2013.
Yoo et al. "Excimer laser deinsulation of Parylene-C on iridium for use in an activated iridium oxide film-coated Utah electrode array," Journal of Neuroscience Methods, 215 (2013) 78-87.
An Office Action dated Mar. 3, 2015, which issued during the prosecution of U.S. Appl. No. 13/148,461.
An Office Action dated Feb. 5, 2015, which issued during the prosecution of U.S. Appl. No. 14/199,462.
An Office Action dated Apr. 14, 2015, which issued during the prosecution of U.S. Appl. No. 14/018,850.
An Office Action dated Feb. 3, 2014, which issued during the prosecution of U.S. Appl. No. 13/683,158.
An invitation to pay additional fees that issued in PCT/IB2014/067417.
An invitation to pay additional fees that issued in PCT/IB2015/050224.
An EP search report dated Feb. 20, 2015 that issued in EP 12782462.1.
ISR and the Written Opinion issued on Jun. 30, 2015 in PCT/IB2014/067417.
ISR and the Written Opinion issued on Jun. 30, 2015 in PCT/IB2015/050224.
Office Action that issued on Aug. 10, 2015 in U.S. Appl. No. 13/827,919.
Office Action that issued on Aug. 20, 2015 in U.S. Appl. No. 14/160,314.

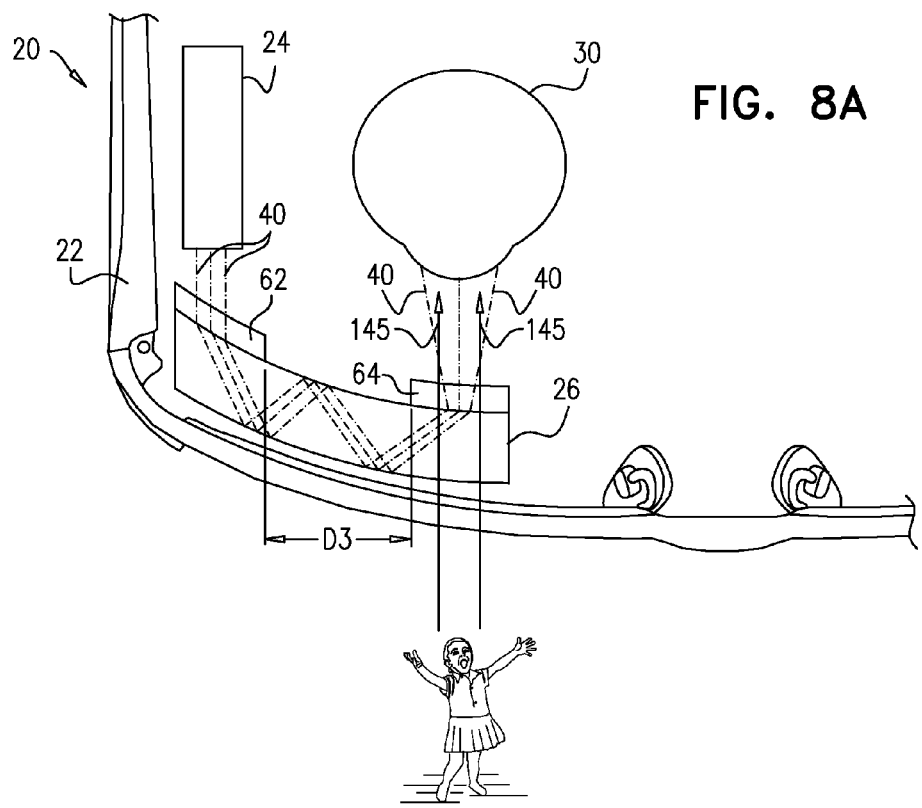
FIG. 8A
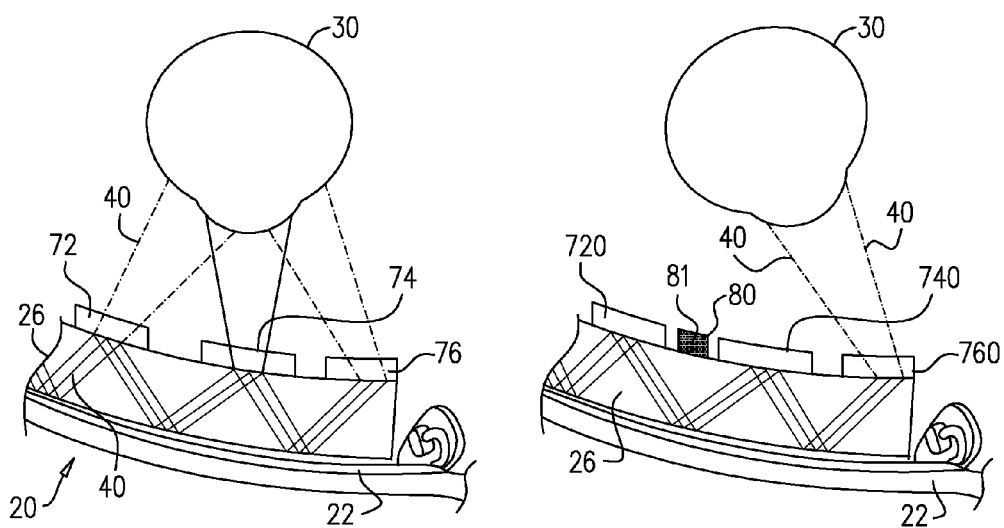
FIG. 8B
FIG. 8C

WEARABLE APPARATUS FOR DELIVERY OF POWER TO A RETINAL PROSTHESIS

FIELD OF THE APPLICATION

Applications of the present invention relate generally to powering of an implantable medical device, and specifically to supplying power to a retinal prosthesis.

BACKGROUND OF THE APPLICATION

Retinal malfunction, due to degenerative retinal diseases, is a leading cause of blindness and visual impairment. Implantation of a retinal prosthesis is a technology for restoring some useful vision in individuals suffering from retinal-related blindness.

Implantable medical devices, e.g., a retinal prosthesis, typically require a source of energy in order to function. Battery-less, wireless power transfer technologies provide a useful way to power an implantable medical device.

SUMMARY OF APPLICATIONS

Some applications of the present invention comprise apparatus comprising an extraocular device having an eyeglasses frame, which is placed in front of an eye of a subject. A power source, e.g., a laser, is coupled to the eyeglasses frame and emits a beam of light that is outside of 380-750 nm (e.g., an infrared beam of light). The beam of light is typically configured to power an intraocular device which is implanted in the subject's eye. In accordance with some applications of the present invention, the extraocular device is configured to diverge and thus defocus the light beam emitted from the power source, such that a wide defocused light beam enters the subject's eye.

Typically, a light-guiding element, e.g., a prism, is coupled to the eyeglasses frame, and at least one optical coupling-in element and at least one optical coupling-out element are optically coupled to the light-guiding element. The coupling-in element is positioned such that the beam of light is directed into the light-guiding element via the coupling-in element, and the coupling-in and coupling-out elements are positioned such that the beam diverges from a focal point located within 3 mm of the coupling-out element. Typically, the coupling-in and coupling-out elements are positioned so as to create a defocused spot of light on a retina of the subject, thereby creating wide and typically uniform illumination of a retina of the subject. Other applications are also described.

There is therefore provided in accordance with some applications of the present invention, apparatus including an extraocular device including:

an eyeglasses frame, configured to be placed in front of an eye of a subject;

a power source coupled to the eyeglasses frame and configured to emit a beam of light that is outside of 380-750 nm;

a light-guiding element coupled to the eyeglasses frame; and at least one optical coupling-in element and at least one optical coupling-out element that are optically coupled to the light-guiding element, the coupling-in element being positioned such that the beam of light is directed into the light-guiding element via the coupling-in element, and the coupling-in and coupling-out elements being positioned such that the beam diverges from a focal point located within 3 mm of the coupling-out element.

For some applications, the power source is configured to emit a collimated beam of light.

For some applications, the power source includes a laser.

For some applications, the coupling-in and coupling-out elements are positioned so as to create a defocused spot of light on a retina of the subject.

For some applications, the power source is configured to emit the beam of light in the range of 750-900 nm.

For some applications, a surface of the light-guiding element is shaped to form the optical coupling-in element.

For some applications, a surface of the light-guiding element is shaped to form the optical coupling-out element.

For some applications, the coupling-in and coupling-out elements are positioned such that the beam diverges at a divergence angle of 5-30 degrees.

For some applications, the extraocular device does not include a camera.

For some applications, the extraocular device is not configured to project an image composed of pixels.

For some applications, the extraocular device is configured to allow ambient light to enter the eye.

For some applications, the light-guiding element includes a prism.

For some applications, the light-guiding element further includes a coating on a surface thereof.

For some applications, the optical coupling-in element is selected from the group consisting of: a lens, a mirror, a grating, and a prism.

For some applications, the light-guiding element includes a prism.

For some applications, the light-guiding element includes an optical fiber.

For some applications, the coupling-out element includes a dichroic mirror.

For some applications, the optical coupling-out element is selected from the group consisting of: a lens, a mirror, a grating, and a prism.

For some applications, the light-guiding element includes a prism.

For some applications, the coupling-out element includes a dichroic mirror.

For some applications, the light-guiding element includes an optical fiber.

For some applications, the light-guiding element includes an optical fiber.

For some applications, the eyeglasses frame includes an eyeglasses lens, and the optical fiber is embedded within the eyeglasses lens.

For some applications, the power source is further configured to direct light out of the power source and into the light-guiding element.

For some applications, the power source includes a pigtail diode.

For some applications, the apparatus includes an intraocular device including:

an energy receiver, configured to receive the beam of light from the power source and to generate a voltage drop in response thereto;

a plurality of stimulating electrodes;

a plurality of photosensors, each photosensor configured to detect photons and to generate a signal in response thereto; and driving circuitry, coupled to the energy receiver and to the photosensors, and configured to receive the signals from the photosensors and to utilize the voltage drop to drive the electrodes to apply currents to a retina of the eye in response to the signals from the photosensors.

There is further provided in accordance with some applications of the present invention, apparatus including an extraocular device including:

an eyeglasses frame, configured to be placed in front of an eye of a subject;

a power source coupled to the eyeglasses frame and configured to emit a collimated beam of light that is outside of 380-750 nm;

an optical element configured to converge the beam to a converging light beam; and a light-guiding element coupled to the eyeglasses frame and positioned to convey the converging beam through at least a portion of the light-guiding element, and arranged such that a diverging beam is conveyed toward the eye of the subject.

For some applications, the optical element includes an optical coupling-in element.

For some applications, the optical coupling-in element is selected from the group consisting of: a lens, a mirror, a grating, and a prism.

For some applications, the optical coupling-in element includes a lens.

For some applications, the light-guiding element includes a prism.

For some applications, the light-guiding element further includes a coating on a surface thereof.

For some applications, the apparatus includes an optical coupling-out element, the light-guiding element is arranged such that the diverging beam is conveyed (a) toward the optical coupling-out element, and (b) from the optical coupling-out element toward eye of the subject.

For some applications, the coupling-out element includes a dichroic mirror.

There is still further provided in accordance with some applications of the present invention, apparatus including an extraocular device including:

an eyeglasses frame, configured to be placed in front of an eye of a subject;

a power source coupled to the eyeglasses frame and configured to emit a beam of light that is outside of 380-750 nm;

a light-guiding element coupled to the eyeglasses frame; and first and second optical coupling-out elements coupled to the light-guiding element and positioned such that:
  (a) the first optical coupling-out element is configured to allow less than all of the light beam to leave the light-guiding element, and
  (b) the second optical coupling-out element is configured to allow at least some of the remaining light to leave the light-guiding element.

For some applications, the first optical coupling-out element is configured to redirect remaining light in the beam to travel through the light-guiding element toward the second optical coupling-out element.

For some applications, the second optical coupling-out element is configured to allow substantially all of the remaining light to leave the light-guiding element.

For some applications, (a) the first optical coupling-out element is configured to allow a first percentage of light from the light beam landing on the first optical coupling-out element to leave the light-guiding element, and
  (b) the second optical coupling-out element is configured to allow a second percentage of light landing on the second optical coupling-out element to leave the light-guiding element, the second percentage being higher than the first percentage.

For some applications, the second percentage is 1.5-2.5 times higher than the first percentage.

For some applications, the second optical coupling-out element is configured to allow substantially 100% of the light landing on the second optical coupling-out element to leave the light-guiding element.

For some applications, the first optical coupling-out element is configured to allow a percentage of light from the light beam landing on the first optical coupling-out element to leave the light-guiding element, and the second optical coupling-out element is configured to allow the same percentage of light from the light beam landing on the second optical coupling-out element to leave the light-guiding element.

For some applications, (a) the first optical coupling-out element is configured to allow 40-60% of the light beam landing on the first optical coupling-out element to leave the light-guiding element, and
  (b) the second optical coupling-out element is configured to allow all of the light beam landing on the second optical coupling-out element to leave the light-guiding element.

For some applications, the first optical coupling-out element is configured to allow 50% of the light beam landing on the first optical coupling-out element to leave the light-guiding element.

For some applications, the apparatus includes a third optical coupling-out element coupled to the light-guiding element, the second optical coupling-out element is configured to redirect at least a portion of the light in the beam to travel through the light-guiding element toward the third optical coupling-out element, and wherein the third optical coupling-out element is configured to allow substantially all of the light landing on the third optical coupling-out element to leave the light-guiding element.

For some applications, (a) the first optical coupling-out element is configured to allow a third of the light beam landing on the first optical coupling-out element to leave the light-guiding element, and
  (b) the second optical coupling-out element is configured to allow a half of the light beam landing on the second optical coupling-out element to leave the light-guiding element.

For some applications, (a) the first optical coupling-out element is configured to allow a first percentage of light from the light beam landing on the first optical coupling-out element to leave the light-guiding element,
  (b) the second optical coupling-out element is configured to allow a second percentage of light landing on the second optical coupling-out element to leave the light-guiding element, and
  (c) the third optical coupling-out element is configured to allow a third percentage of light landing on the third optical coupling-out element to leave the light-guiding element,
  the third percentage being higher than the second percentage, and the second percentage being higher than the first percentage.

There is further provided in accordance with some applications of the present invention, apparatus including an extraocular device including:

an eyeglasses frame, configured to be placed in front of an eye of a subject;

a power source coupled to the eyeglasses frame and configured to emit a beam of light that is outside of 380-750 nm;

a light-guiding element coupled to the eyeglasses frame and positioned to receive the emitted beam of light;

first and second optical coupling-out elements, optically coupled to the light-guiding element;

one or more sensors configured to identify a gaze direction of the subject and to generate a signal in response thereto;

the apparatus configured to, in response to identifying the gaze direction of the subject: (a) determine which of the first and second optical coupling-out elements is in the gaze of the subject, and (b) allow the light beam to leave the light-guiding element toward the eye of the subject through the coupling-out element in the gaze direction.

For some applications, the apparatus includes a switch, configured to receive the signal and in response thereto to switch at least the first coupling-out element between (a) a transmissive mode, in which the first coupling-out element facilitates light from the beam of light leaving the light-guiding element and going toward the eye of the subject and (b) a reflective mode, in which the first coupling-out element facilitates light from the beam of light going toward the second coupling-out element and inhibits light from the beam of light from leaving the light-guiding element and going toward the eye of the subject.

For some applications, the apparatus includes an intraocular device, and the one or more sensors are configured to identify a gaze direction of the subject by receiving a reflection of the beam of light reflected from the intraocular device.

For some applications, the one or more sensors include an infrared camera configured to identify the gaze direction of the subject.

There is further provided in accordance with some applications of the present invention, apparatus including:

an eyeglasses frame, configured to be placed in front of an eye of a subject;

an eyeglasses lens, coupled to the frame; and an optical fiber embedded within the eyeglasses lens and positioned to emit light toward the eye of the subject.

For some applications, the apparatus further includes a power source coupled to the eyeglasses frame and configured to (a) emit a beam of light that is outside of 380-750 nm; and (b) to direct light out of the power source and into the optical fiber.

For some applications, the power source includes a pigtail diode, positioned to direct the light into the fiber.

There is further provided in accordance with some applications of the present invention, apparatus including an extraocular device, including:

an eyeglasses frame, configured to be placed in front of an eye of a subject;

a power source coupled to the eyeglasses frame and configured to emit a beam of light that is outside of 380-750 nm; and a light-guiding element coupled to the eyeglasses frame: (a) a thickness of the light-guiding element being less than 4 mm at a site of the light-guiding element from which the beam of light exits the light-guiding element, and (b) a length of the light-guiding element, along which the thickness is less than 4 mm, being at least 10 mm.

For some applications, an area of the light-guiding element, along which the thickness is less than 4 mm, is at least 200 mm2.

There is further provided in accordance with some applications of the present invention, apparatus including an extraocular device including:

an eyeglasses frame, configured to be placed in front of an eye of a subject;

a power source coupled to the eyeglasses frame and configured to emit a beam of light that is outside of 380-750 nm;

a light-guiding element coupled to the eyeglasses frame; and first and second optical coupling-out elements coupled to the light-guiding element and positioned such that there is a space of at least 1 mm distance between the optical coupling-out elements, the space not containing an optical coupling-out element.

For some applications, the power source is configured to direct the light beam at the first and the second coupling element.

For some applications, the extraocular device does not include more than 10 coupling-out elements.

There is further provided in accordance with some applications of the present invention, apparatus including an extraocular device including:

an eyeglasses frame, configured to be placed in front of an eye of a subject;

a plurality of power sources coupled to the eyeglasses frame, each power source configured to emit a beam of light that is outside of 380-750 nm;

a light-guiding element coupled to the eyeglasses frame and configured to receive the light emitted from the plurality of power sources; and a plurality of optical coupling-out elements optically coupled to the light-guiding element, each coupling-out element positioned to receive the beam of light from a respective one of the plurality of power sources and to allow the light beam to leave the light-guiding element toward the eye of the subject.

For some applications, the apparatus includes one or more sensors configured to identify a gaze direction of the subject and to generate a signal in response thereto, and the apparatus is configured to, in response to identifying the gaze direction of the subject: (a) determine which one of the plurality of optical coupling-out elements is in the gaze of the subject, and (b) allow the light beam from the one of the plurality of optical coupling-out elements to leave the light-guiding element toward the eye of the subject.

There is further provided in accordance with some applications of the present invention, Apparatus including an extraocular device including:

an eyeglasses frame, configured to be placed in front of an eye of a subject;

a power source coupled to the eyeglasses frame and configured to emit a beam of light that is outside of 380-750 nm;

a light-guiding element coupled to the eyeglasses frame;

a plurality of optical coupling-out elements optically coupled to the light-guiding element, each coupling-out element positioned to allow the light beam to leave the light-guiding element, toward the eye of the subject; and a beam director coupled to the power source and configured to direct the beam of light to each of the optical coupling-out elements.

For some applications, the beam director includes one or more beam-splitters.

For some applications, the beam director includes a modulator, configured to non-simultaneously direct the beam of light to each of the optical coupling-out elements.

For some applications, the apparatus includes one or more sensors configured to identify a gaze direction of the subject and to generate a signal in response thereto, and the apparatus is configured to, in response to identifying the gaze direction of the subject: (A) determine which one of the plurality of optical coupling-out elements is in the gaze of the subject, and (B) cause the modulator (i) to direct the light beam to leave the light-guiding element toward the eye through a coupling-out element that is situated in the gaze of the subject, and (ii) to inhibit the light beam from leaving the light-guiding element toward the eye through a coupling-out element not situated in the gaze of the subject.

The present invention will be more fully understood from the following detailed description of applications thereof, taken together with the drawings, in which:

BRIEF DESCRIPTION OF THE DRAWINGS

FIGS. 8A-C are schematic illustrations of apparatus comprising an extraocular device, in accordance with some applications of the present invention;

DETAILED DESCRIPTION OF APPLICATIONS

Figure 1A:
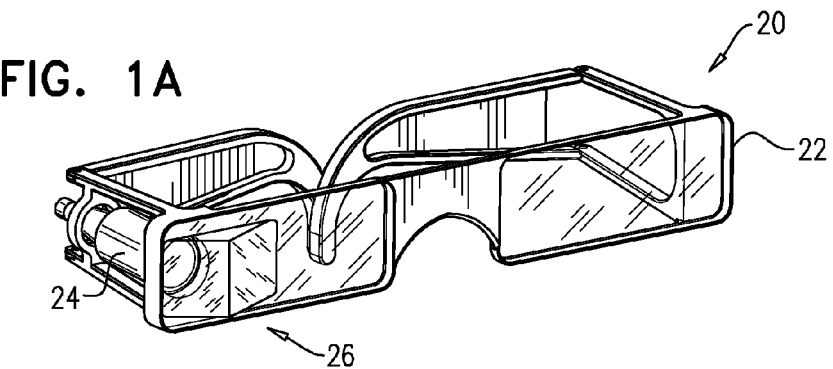
FIGS. 1A-B are schematic illustrations of apparatus comprising an extraocular device, in accordance with some applications of the present invention.
Figure 1B:
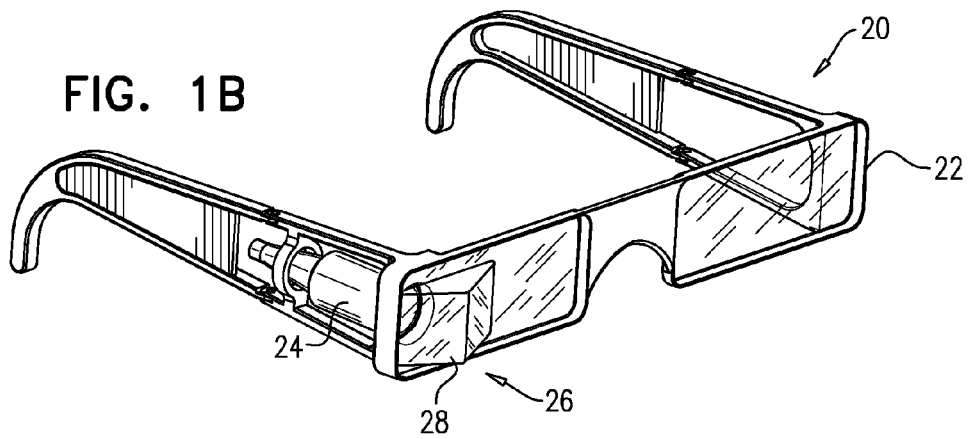

Reference is made to FIGS. 1A-B and 2A-C. FIGS. 1A-B are schematic illustrations of apparatus comprising an extraocular device 20, in accordance with some applications of the present invention. Extraocular device 20 typically comprises an eyeglasses frame 22, which is placed in front of an eye of a subject. A power source 24, e.g., a laser, is coupled to frame 22 and emits a beam of light, e.g., a collimated beam, a diverging beam, or a converging beam, that is outside of the visible light range, e.g., outside 380-750 nm. For example, the power source may be configured to emit the beam of light in the range of 750-900 nm. Typically the beam of light is configured to power an intraocular device, e.g., a retinal prosthesis, which is implanted in the subject's eye. The intraocular device is typically configured to receive the beam of light from the power source and to generate a power signal to power the intraocular device.

Typically, a light-guiding element 26, e.g., a prism (as shown) or an optical fiber (FIG. 9), is coupled to eyeglasses frame 22. Typically, power source 24 is configured to direct light out of the power source and into light-guiding element 26. Light-guiding element 26 may or may not comprise a coating on a surface thereof.

It is noted that extraocular device 20 does not comprise a camera, and does not project an image composed of pixels toward the subject's eye. Additionally, extraocular device generally does not obscure the visual field of the subject and is configured to allow ambient light to enter the eye of the subject, such that an image of an ambient scene can form on the retinal prosthesis.

It is further noted that the light beam, while not projecting image data, can be modulated to regulate operation parameters of the intraocular device (e.g., by emitting the light beam as a series of pulses which provide power and also encode data).

Figure 2A:
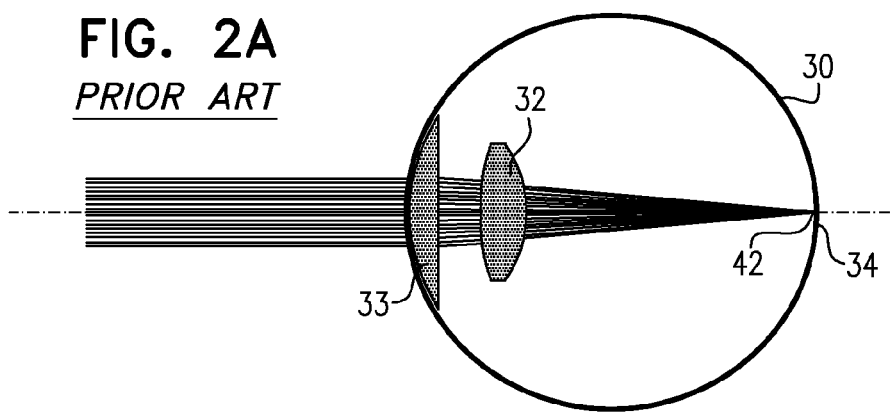
FIG. 2A is a schematic illustration of ray traces, as are known in the art.

FIG. 2A is a schematic illustration of light from an ambient scene naturally entering eye 30 and becoming focused, due to natural focusing mechanisms of the eye, on a focus point 42 on a retina 34.

Figure 2B:
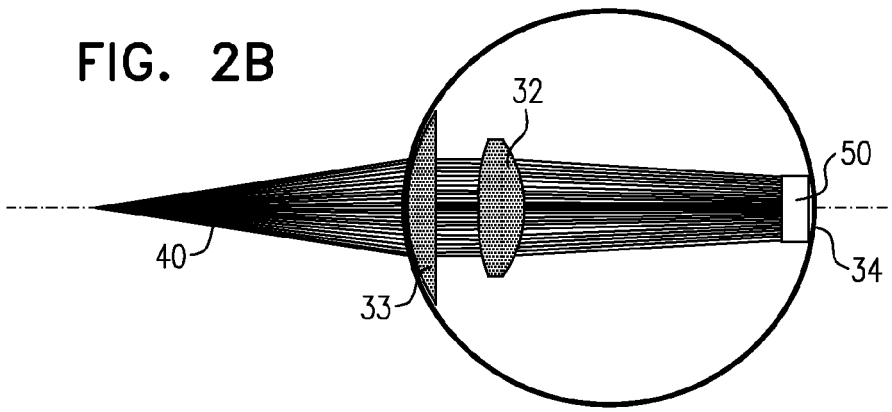
FIGS. 2B-C are schematic illustrations of ray traces produced using the apparatus of FIGS. 1A-B, in accordance with some applications of the present invention.
Figure 2C:
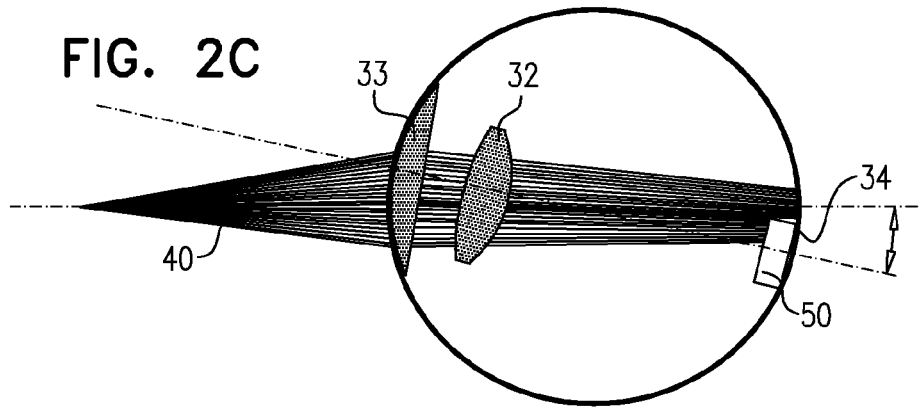

FIGS. 2B-C are schematic illustrations of ray traces produced using the apparatus of FIGS. 1A-B, in accordance with some applications of the present invention. As shown in FIGS. 2B-C, a retinal prosthesis 50 is implanted in eye 30 of the subject, typically but not necessarily, in an epi-retinal position. Retinal prosthesis 50 is typically configured to receive light beam 40 from power source 24 (shown in FIG. 1A) and to generate a power signal to power components of prosthesis 50. Creating wide, defocused illumination of retina 34 typically improves the effectiveness of power supply to prosthesis 50 and additionally enhances the safety of prosthesis 50. Due to safety concerns it is generally advisable to limit the intensity (i.e., power per unit area) of the power contacting delicate eye structures (e.g., cornea 33 and retina 34). By defocusing beam 40, transmitted power is spread over a larger area, thereby reducing the intensity while generally transmitting the same amount of power.

Additionally, projecting a wide, defocused beam 40 onto retina 34 typically improves the effectiveness of power supply to prosthesis 50 during saccadic eye movement. Due to saccadic eye movement, beam 40 is not continuously perfectly aimed at the retina 34. As shown in FIG. 2C, by having a wide, defocused illumination of retina 34, at least a portion of prosthesis 50 is illuminated, i.e., powered by beam 40, during saccadic eye movement. Thus, generally continuous power is provided to prosthesis 50.

Figure 3:
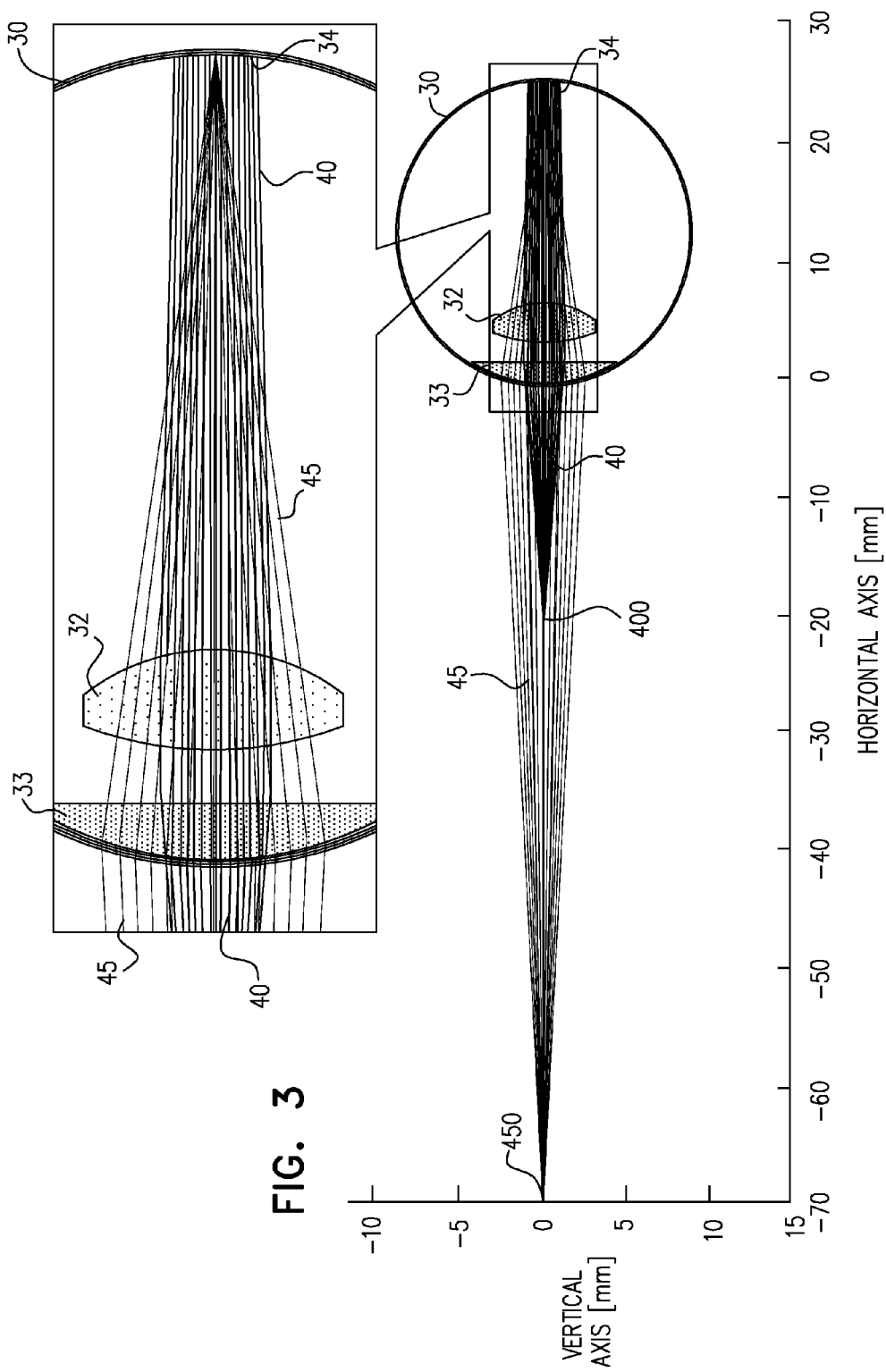
FIG. 3 is a graph representing various focal distances, useful in understanding the apparatus of FIGS. 1A-B.

Reference is made to FIG. 3. A young human eye is typically capable of focusing through accommodation, which is the process by which the eye changes optical power to maintain a clear focus on an object as its distance varies. Typically, the minimum focusing distance for a human is 7 cm. Thus a beam 45 with a focal point 450 of at least 7 cm or greater from cornea 33, is focused onto the retina, as shown in FIG. 3. Generally, an object located at a distance of less than 7 cm from cornea 33 cannot be focused by natural mechanisms of the eye. In order to ensure that a defocused beam 40 enters eye 30, in accordance with some applications of the present invention, device 20 is configured such that a focal point 400 of beam 40 is located at a distance that is 1-5, e.g., 2 cm, from cornea 33.

Figure 4:
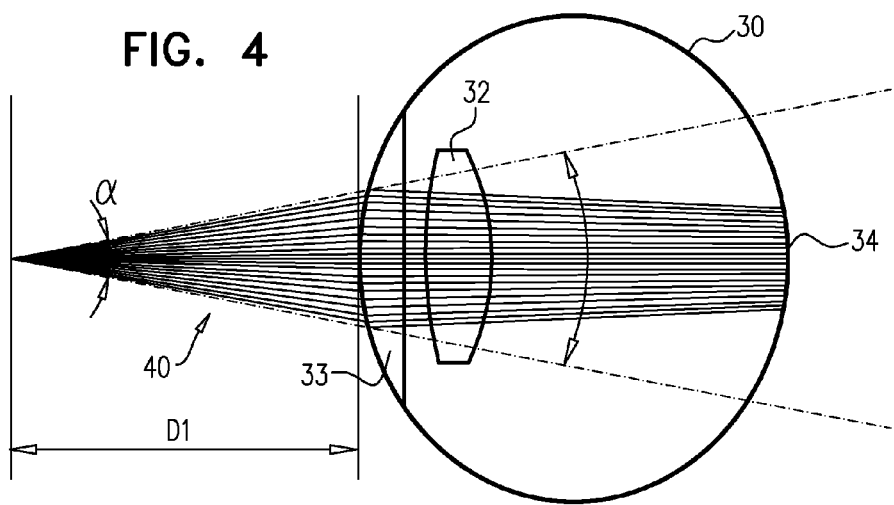
FIG. 4 is a schematic illustration of a typical divergence angle of a beam, achieved in accordance with some applications of the present invention.

Reference is made to FIG. 4, which is a schematic illustration of a typical divergence angle alpha of beam 40, in accordance with some applications of the present invention. Device 20 is typically positioned such that beam 40 diverges at divergence angle alpha of 5-30 degrees, from a focus point (provided by the optics of device 20) that is a distance D1 that is 1-5 cm from cornea 33. Typically, the divergence angle generally provides that the beam is transmitted through the entire pupil, increasing the amount of power transmitted to the retinal prosthesis.

Figure 5A:
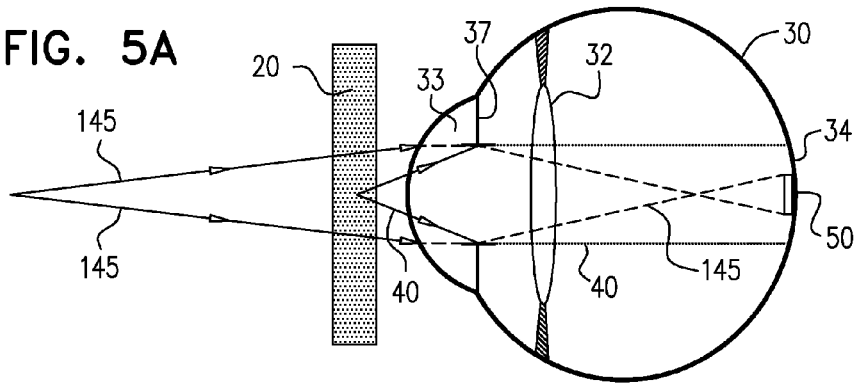
FIG. 5A is a schematic illustration of a system for use in the extraocular device of FIGS. 1A-B, in accordance with some applications of the present invention.
Figure 5B:
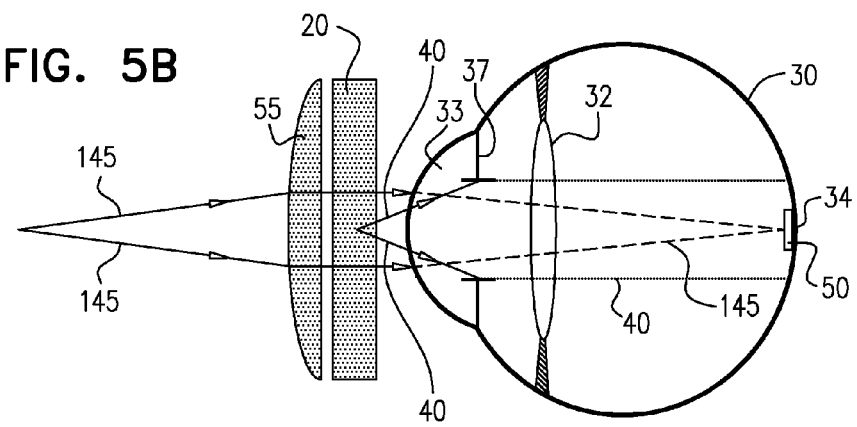
FIG. 5B is a schematic illustration of a corrective lens system for use in the extraocular device of FIGS. 1A-B, in accordance with some applications of the present invention.

Reference is made to FIGS. 5A-B. Some applications of the present invention are configured for use with a corrective optical lens 55. Corrective optical lens 55 is typically used for vision correction in the case of common vision disorders such as myopia, hyperopia, astigmatism, or presbyopia. As noted hereinabove, extraocular device 20 generally does not obscure the visual field of the subject and is configured to allow ambient light rays 145 to enter eye 30, such that visible light emanating from objects is received by prosthesis 50. Additionally, beam 40 emitted from extraocular device 20 (e.g., an infrared light beam emitted from power source 24), does not disrupt ambient light, e.g., visible ambient light rays 145, from entering eye 30. Corrective optical lens 55 is typically used to facilitate proper receiving of focused ambient light rays by prosthesis 50. Typically, in a healthy subject, light passes through cornea 33 and pupil of iris 37, is bent or refracted by lens 32, and comes to a point or focus on retina 34, where the image is formed.

FIG. 5A is a schematic illustration of eye 30 of a subject suffering from both retinal malfunction and myopia. As shown, retinal prosthesis 50 is implanted onto retina 34 for treatment of the retinal malfunction. In accordance with some applications of the present invention, light beam 40 from device 20 is emitted towards the eye and lands on retina 34 and prosthesis 50 as a wide defocused beam to power prosthesis 50. Visible light rays 145 enter the eye and, due to myopia, are focused in front of retina 34 and prosthesis 50, rather than on the retina and the prosthesis. Corrective optical lens 55, shown in FIG. 5B, is typically placed in front of eye 30 of the subject to correct the myopia and thus achieve focusing of visible rays 145 and a focused image on prosthesis 50.

It is noted that as shown in FIG. 5B, corrective optical lens 55 is typically coupled to device 20, such that beam 40 does not pass through corrective optical lens 55.

Figure 6:
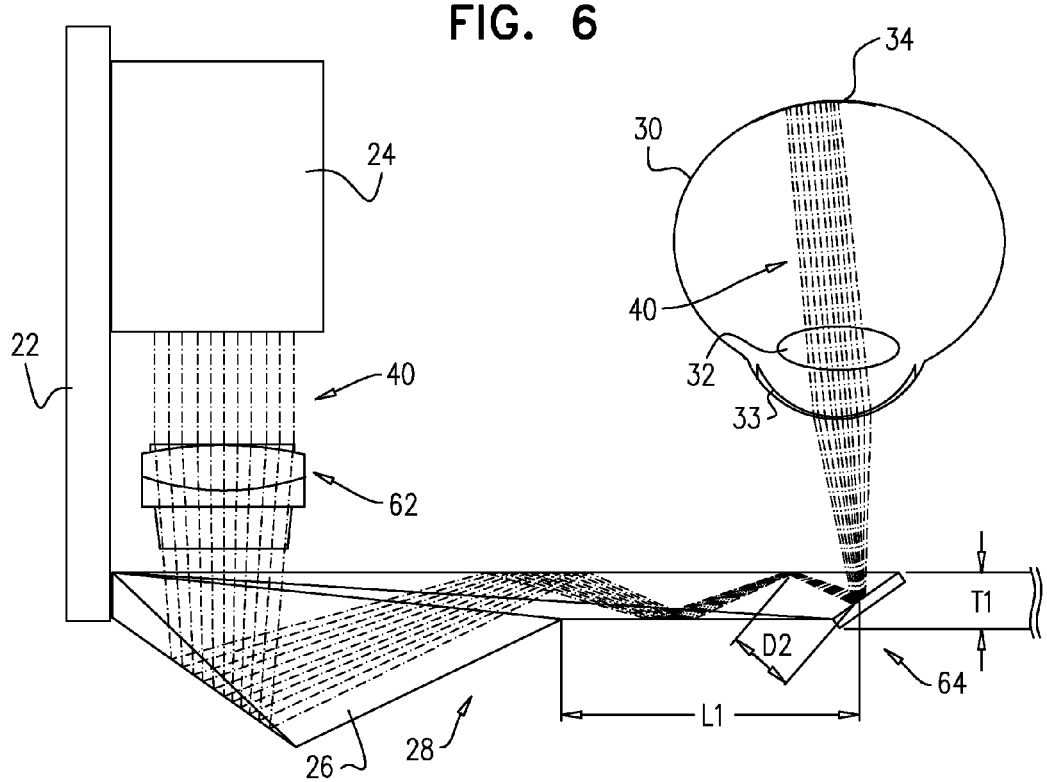
FIG. 6 is a schematic illustration of apparatus comprising an extraocular device, in accordance with some applications of the present invention.

Reference is made to FIG. 6. For some applications, a light-guiding element 26, e.g., a prism 28 is coupled to eyeglasses frame 22. An optical element, e.g. a coupling-in element 62, is positioned to converge beam 40 emitted from power source 24 to a converging light beam. Prism 28 is shaped and positioned to convey the converging beam through at least a portion of the prism 28, and arranged such that a diverging beam is conveyed toward the eye of the subject. For some applications, an optical coupling-out element 64, e.g., a dichroic mirror, is optically coupled to prism 28, and the prism is arranged such that the diverging beam is conveyed (a) toward optical coupling-out element 64, and (b) from optical coupling-out element 64 toward eye 30 of the subject, to project a defocused beam 40 on retina 34.

Coupling-in element 62 is positioned such that the beam of light is directed into light-guiding element 26 via the coupling-in element. Coupling-in and coupling-out elements 62 and 64 are positioned such that the beam diverges from a focal point located at a distance D2 that is typically within 3 mm of the coupling-out element, to create a defocused light beam which enters the eye. Light-guiding element 26 typically has a thickness T1 that is less than 4 mm (e.g., 2-4 mm) at a site of the light-guiding element from which the beam of light exits the light-guiding element. It is noted that the thickness of less than 4 mm of the light-guiding element is maintained also for applications in which a corrective lens 55 is optically coupled to the light-guiding element (as shown in FIG. 5B). Typically, but not necessarily, an optical separation (e.g., an air gap and/or a dichroic mirror) is placed between the light-guiding element and the corrective lens. In any case, the thickness of light-guiding element 26 itself is typically less than 4 mm, regardless of any additional thickness provided by corrective lens 55.

Light-guiding element 26 typically has the above-mentioned thickness T1 that is less than 4 mm over a significant portion of its surface. For example, this portion of the surface may have a length L1 that is at least 10 mm. It is noted that L1 is shown extending in a lateral (i.e., left-right) direction. This portion of the surface of light-guiding element 26 typically has a length L1 that is at least 10 mm extending in the vertical direction, as well. Thus, an area of light-guiding element 26, along which the thickness is less than 4 mm, is typically at least 100 mm2, e.g., at least 200 mm2.

Optical coupling-in and coupling-out elements 62 and 64 typically comprise a lens, a mirror, a grating, or a prism. For some applications, the coupling-out element comprises a dichroic mirror (e.g., as shown in FIG. 6). For some applications, a surface of light-guiding element 26 is shaped to form the optical coupling-in element and/or the coupling-out element. Alternatively or additionally, elements 62 and/or 64 are structurally separate from (but optically coupled to) light-guiding element 26. It is noted that the use of any combination of coupling-in elements and coupling-out elements as described herein is within the scope of the present invention.

For some applications, as described hereinbelow with reference to FIGS. 8A-C and 10A-B, more than one, but typically not more than ten, coupling-out element are optically coupled to guide 26. The optical coupling-out elements are positioned such that there is a space, D3, of at least 1 mm distance between the optical coupling-out elements, the space not containing an optical coupling-out element. Accordingly, due to the number and spacing of the coupling-out elements, they do not function as pixels for projecting an image towards the eye.

Figure 7:
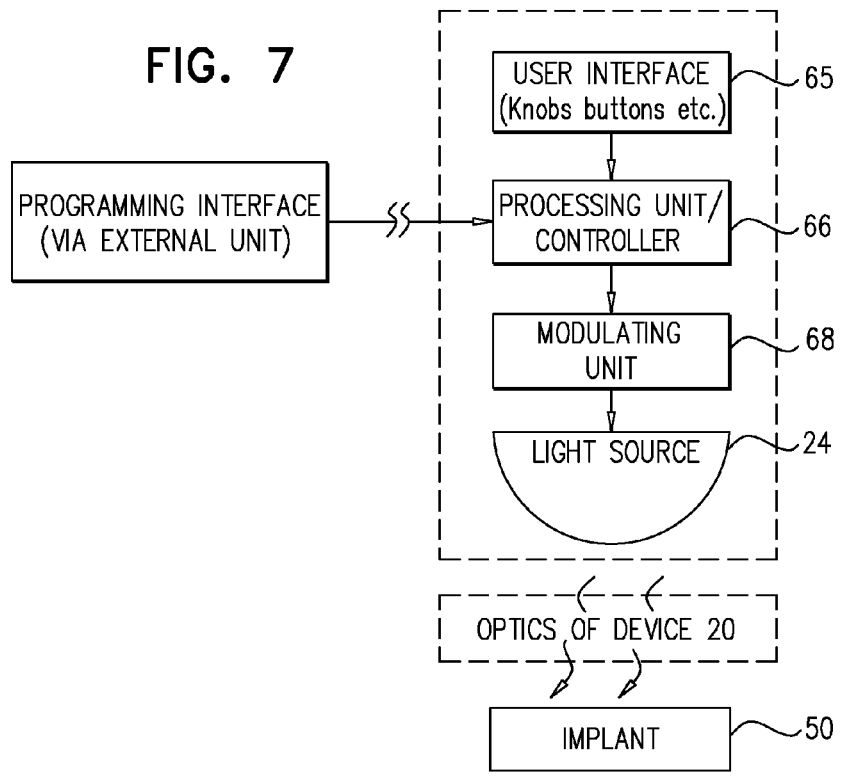
FIG. 7 is a block diagram of components of apparatus comprising an extraocular device, in accordance with some applications of the present invention.

Reference is made to FIG. 7, which is a block diagram of components of apparatus comprising an extraocular device, in accordance with some applications of the present invention. In some applications of the present invention, external device 20 comprises a user interface element 65 (e.g., a dial, switch, or button), a controller 66 and a modulating unit 68, coupled to eyeglasses frame 22, allowing the subject to interactively control characteristics of the beam emitted from power source 24, e.g., by using the beam to send non-image data to the retinal prosthesis, in addition to transmitting power to the prosthesis.

Reference is made to FIG. 8A, which is a schematic illustration of apparatus comprising extraocular device 20 in accordance with some applications of the present invention. As shown, power source 24, typically an infrared light emitter, is coupled to eyeglasses frame 22 and emits light beam 40 toward light-guiding element 26, e.g., a waveguide or prism. Light-guiding element 26 can be either curved or straight, and typically, as noted hereinabove, has a thickness of 1-4 mm, e.g., 2-4 mm. Light-guiding element 26 is typically coupled to eyeglasses frame 22 by similar means by which conventional lenses are mounted onto eyeglasses frames. The light-guiding element typically directs beam 40 by means of total internal reflection, until the beam leaves element 26.

Coupling-in element 62 is optically coupled to light-guiding element 26 and is positioned such that beam 40 is directed into light-guiding element 26 via the coupling-in element. Additionally, optical coupling-out element 64 is optically coupled to light-guiding element 26, and is positioned such that beam 40 is directed out of element 26 and into eye 30 of the subject via the coupling-out element.

Coupling-in and out elements 62 and 64 typically function in order to optimize guiding of beam 40 into and out of guiding element 26. Examples for suitable coupling-in and coupling-out elements include lenses, gratings, prisms and surface coatings, as well as other passive or active elements. Coupling-in and coupling-out elements 62 and 64 are typically used to optimize a shape of beam 40, to reduce light loss when beam 40 enters and leaves guiding element 26, and to direct beam 40 to an appropriate position in eye 30.

In accordance with some applications of the present invention, FIG. 8A shows a wide, defocused, diverging light beam 40 entering eye 30 to power prosthesis 50 (e.g., shown in FIG. 2B). Additionally, as shown, extraocular device 20 does not interfere with visible image 145 from entering eye 30 to form an image.

Reference is made to FIG. 8B, which is a schematic illustration of apparatus comprising extraocular device 20 in accordance with some applications of the present invention. Extraocular device 20 is configured to simultaneously emit light from a plurality of coupling-out elements, each coupled to the light-guiding element at a discrete location, such that during periods of movement of the eye, beam 40 is generally continuously projected onto prosthesis 50. It is noted that coupling-out elements 72, 74 and 76 shown in FIG. 8B and the use thereof are the same as coupling-out elements 62 and 64, except for differences described below.

For some applications, a first optical coupling-out element 72 and a second optical coupling-out element 74 are optically coupled to light-guiding element 26 and positioned such that: (a) first optical coupling-out element 72 allows less than all of light beam 40 to leave light-guiding element 26, and (b) second optical coupling-out element 74 allows at least some of the remaining light (in some cases, substantially all of the remaining light) to leave light-guiding element 26. Typically, first optical coupling-out element 72 redirects remaining light in beam 40 to travel through light-guiding element 26 toward second optical coupling-out element 74.

For some applications, first optical coupling-out element 72 allows a first percentage, e.g. 40-60%, e.g., 50%, of light from light beam 40 landing on the first optical coupling-out element to leave light-guiding element 26, and second optical coupling-out element 74 allows a second percentage, e.g., substantially 100% of light landing on the second optical coupling-out element, to leave light-guiding element 26. Typically, the second percentage is higher than the first percentage, e.g., 1.5-2.5 times higher than the first percentage. For other applications, the second percentage is the same as the first percentage. Typically, each optical coupling-out element has suitable optical properties that facilitate the various percentages of transmission.

For some applications, as shown in FIG. 8B, a third optical coupling-out element 76 is coupled to light-guiding element 26, and second optical coupling-out element 74 redirects at least a portion of the light in beam 40 to travel through light-guiding element 26 toward third optical coupling-out element 76. Typically, third optical coupling-out element 76 allows substantially all of the light landing on the third optical coupling-out element to leave light-guiding element 26.

For some such applications, first optical coupling-out element 72 allows a third of light beam 40 landing on the first optical coupling-out element to leave light-guiding element 72, and second optical coupling-out element 74 allows a half of light beam 40 landing on the second optical coupling-out element to leave the light-guiding element. Typically, third optical coupling-out element 76 allows substantially all of the light landing on the third optical coupling-out element to leave light-guiding element 26.

For some applications, (a) first optical coupling-out element 72 allows a first percentage of light from light beam 40 landing on the first optical coupling-out element to leave light-guiding element 26, (b) second optical coupling-out element 74 allows a second percentage of light landing on the second optical coupling-out element to leave light-guiding element 26, and (c) third optical coupling-out element 76 allows a third percentage of light landing on the third optical coupling-out element to leave the light-guiding element. Typically, the third percentage is higher than the second percentage, and the second percentage is higher than the first percentage.

Reference is made to FIG. 8C. For some applications, one or more sensors 80 e.g., eye-tracking sensors, are coupled to light-guiding element 26 or elsewhere on device 20, and identify a gaze direction of the subject and generate a signal in response thereto. Typically, in response to identifying the gaze direction of the subject, extraocular device 20 determines which of first and second optical coupling-out elements 720 and 740 (or, for some cases, also a third coupling-out element 760) are generally in the gaze of the subject, and allows light beam 40 (from power source 24) to leave light-guiding element 26 toward eye 30 through the coupling-out element situated in the gaze of the subject. In this manner, device 20 increases the effectiveness of power supply to implantable prosthesis 50, by generally directing a larger portion of a smaller beam 40 toward prosthesis 50 than in applications of the present invention in which a larger beam 40 is utilized to provide power to prosthesis 50 regardless of gaze direction.

For some applications, extraocular device 20 comprises a switch 81, disposed within a housing of sensor 80 or elsewhere in device 20. Switch 81 receives the signal generated in response to identifying the gaze direction of the subject and in response to receiving the signal, switches at least first coupling-out element 720 between (a) a transmissive mode, in which the first coupling-out element facilitates light from beam 40 of light leaving light-guiding element 26 and going toward eye 30 and (b) a reflective mode, in which first coupling-out element 720 facilitates light from beam 40 of light going toward second coupling-out element 740 and inhibits light from beam 40 of light from leaving light-guiding element 26 and going toward eye 30.

For some applications, one or more sensors 80 are configured to identify a gaze direction of the subject by receiving a reflection of beam 40 which is reflected from intraocular prosthesis 50 (shown in FIGS. 2B-C).

For some applications, one or more sensors 80 comprise an infrared camera configured to identify the gaze direction of the subject. It is noted that the infrared camera identifies and tracks the gaze of the subject, but typically does not image a scene and does not project an image toward the subject's eye.

It is noted that coupling-out elements 720, 740 and 760 shown in FIG. 8C are the same as coupling-out elements 62 and 64, except for differences described hereinabove with reference to FIG. 8C.

Figure 9:
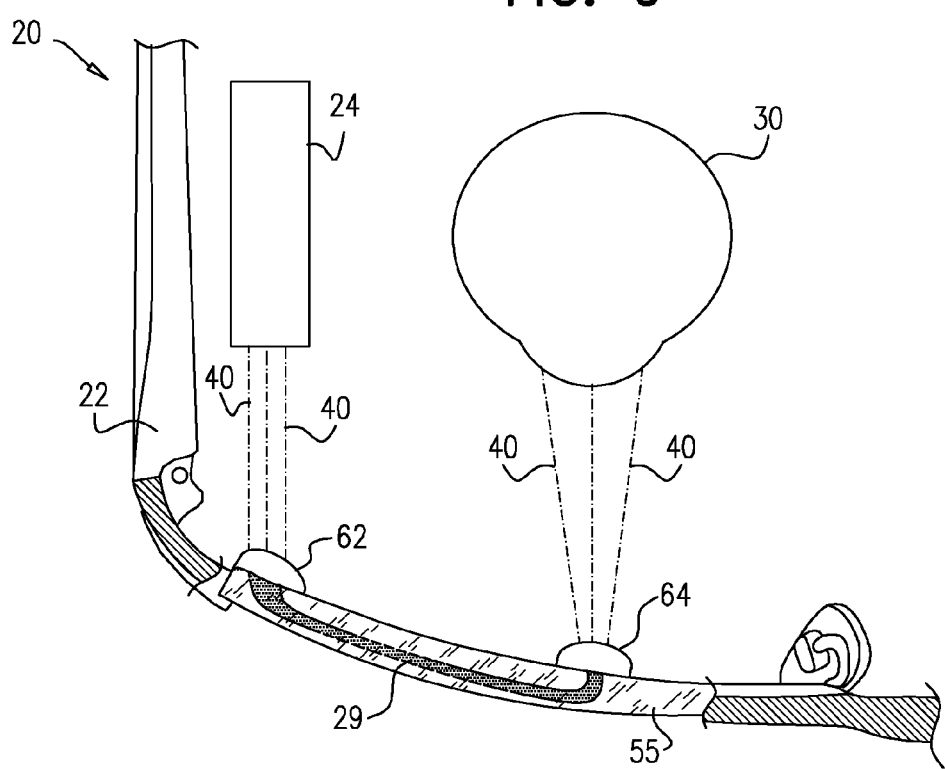
FIG. 9 is a schematic illustration of apparatus comprising an extraocular device, in accordance with some applications of the present invention.

Reference is made to FIG. 9, which is a schematic illustration of extraocular device 20, in accordance with some applications of the present invention. For some applications, light-guiding element 26 comprises an optical fiber 29. Typically, for such applications, an eyeglasses lens 55 is coupled to frame 22, and optical fiber 29 is embedded within the eyeglasses lens and positioned to emit light toward eye 30 of the subject.

Typically, power source 24, which is coupled to eyeglasses frame 22, emits a beam of light 40 that is outside of 380-750 nm. Extraocular device 20 is configured to direct light beam 40 out of power source 24 and into optical fiber 29. For some applications directing of light beam 40 into optical fiber 29 is facilitated by optical coupling-in element 62 and/or light beam 40 leaves fiber 29 via optical coupling-out element 64.

For some applications, power coupling-in element 62 comprises a pigtail diode, positioned to direct light beam 40 into fiber 29.

For some applications, as shown in FIG. 9, beam 40 enters optical fiber 29 through optical coupling-in element 62 as a collimated beam, and leaves optical fiber 29 through optical coupling-out element 64 as a diverging beam. Accordingly, beam 40 enters eye 30 as a defocused beam. Alternatively, beam 40 leaving coupling-out element 64 converges to a point in space between element 64 and eye 30, and subsequently diverges as it enters the eye (configuration not shown).

It is noted that light-guiding element 26 may comprise an optical fiber 29 also in other configurations, e.g., as shown with reference to FIGS. 6, 8A-C, and 10A-B.

Figure 10A:
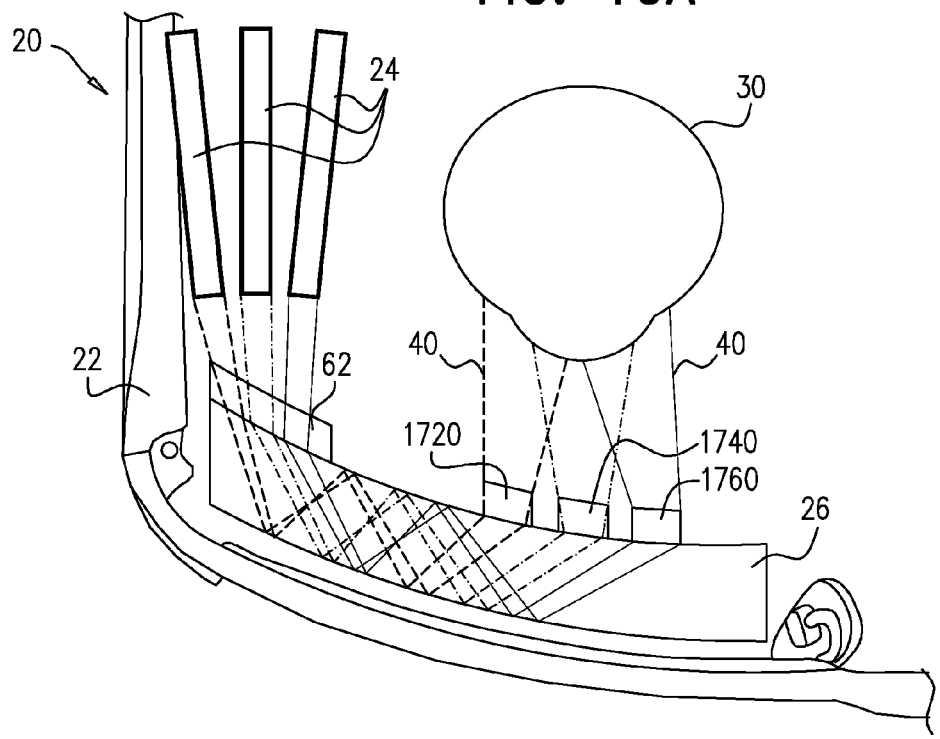
FIGS. 10A-B are schematic illustrations of apparatus comprising an extraocular device, in accordance with some applications of the present invention.

Reference is made to FIG. 10A, which is a schematic illustration of extraocular device 20 in accordance with some applications of the present invention. As shown in FIG. 10A, extraocular device 20 is configured to apply power to the prosthesis through a plurality of optical coupling-out elements, such that retinal prosthesis 50 (shown in FIGS. 2B-C) is generally continuously powered during a period of eye movements. For some such applications, extraocular device 20 comprises a plurality of power sources 24, each configured to emit light that enters light-guiding element 26 through optical coupling-in element 62 and leaves light-guiding element 26 through a discrete optical coupling-out element.

Accordingly, extraocular device 20 comprises optical coupling-out elements 1720, 1740, and 1760, which are optically coupled to discrete locations of element 26 such that when a gaze of the subject changes, power still enters eye 30 through at least one of the optical coupling-out elements. It is noted that coupling-out elements 1720, 1740 and 1760 shown in FIGS. 10A-B are the same as coupling-out elements 62 and 64, except for differences described herein with reference to FIGS. 10A-B.

For some applications, non-visible light of beam 40 is continuously emitted from the plurality of light sources 24 towards light-guiding element 26. For other applications, extraocular device 20 comprises one or more eye-tracking sensors (e.g., as shown in FIG. 8C), which are coupled to light-guiding element 26 or elsewhere on device 20, and identify a gaze direction of the subject and generate a signal in response thereto. Typically, in response to identifying the gaze direction of the subject, extraocular device 20 determines which of optical coupling-out elements 1720 and/or 1740 and/or 1760 are generally in the gaze of the subject, and causes light beam 40 to leave light-guiding element 26 toward eye 30 through the coupling-out element situated in the gaze of the subject, and typically not through a coupling-out element not situated in the gaze of the subject.

Figure 10B:
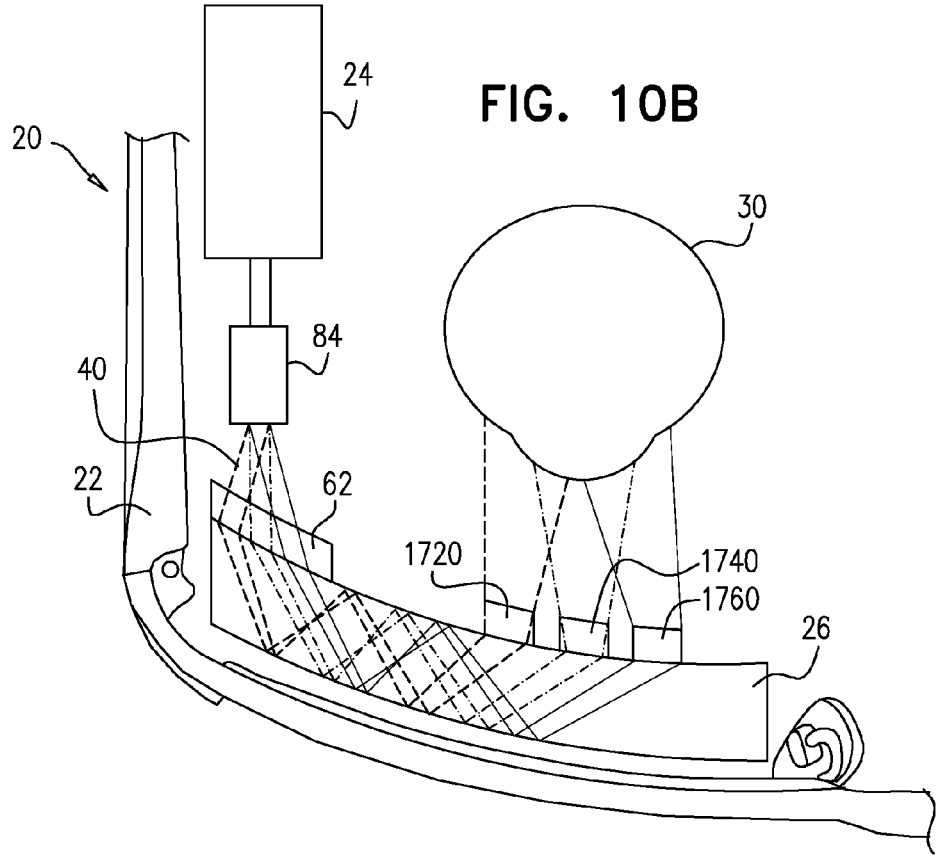

Reference is made to FIG. 10B. For some applications, as shown in FIG. 10B, extraocular device 20 comprises a single power source 24 and a beam director 84, which is configured to direct beam 40 to each of the optical coupling-out elements. For example, beam director 84 may comprise a modulator, e.g., an acousto-optic modulator, configured to diffract and shift the frequency of light to create multiple beams 40 and achieve an effect of multiple non-simultaneous beams, as described hereinabove with reference to FIG. 10A. Alternatively, device 20 comprises one or more sensors (e.g., as shown in FIG. 8C), which are coupled to light-guiding element 26 or elsewhere on device 20, and identify a gaze direction of the subject and generate a signal in response thereto. Typically, in response to identifying the gaze direction of the subject, extraocular device 20 determines which one of the plurality of optical coupling-out elements 1720 and/or 1740 and/or 1760 are generally in the gaze of the subject, and causes modulator 84 to direct a light beam 40 to leave light-guiding element 26 toward eye 30 through the coupling-out element situated in the gaze of the subject, and typically inhibit the light beam from leaving the light-guiding element toward the eye through a coupling-out element not situated in the gaze of the subject.

For some applications, beam director 84 is passive, e.g., it may comprise a beam-splitter, which simultaneously directs beam 40 to each of the coupling-out elements.

Reference is made to prosthesis 50 (as shown for example in FIGS. 2B-C and 5A-B). Prosthesis 50 typically comprises an intraocular device. The intraocular device typically comprises an energy receiver, which receives the beam of light from the power source and generates a voltage drop in response thereto; a plurality of stimulating electrodes; a plurality of photosensors, which detect photons and generate a signal in response thereto; and driving circuitry, coupled to the energy receiver and to the photosensors, which receives the signals from the photosensors and utilizes the voltage drop to drive the electrodes to apply currents to retina 34 in response to the signals from the photosensors.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising an extraocular device comprising:
   an eyeglasses frame, configured to be placed in front of an eye of a subject;
   a power source coupled to the eyeglasses frame and configured to emit a beam of light that is outside of 380-750 nm;
   a light-guiding element coupled to the eyeglasses frame; and
   at least one optical coupling-in element and at least one optical coupling-out element that are optically coupled to the light-guiding element,
      the coupling-in element being positioned such that the beam of light is directed into the light-guiding element via the coupling-in element, and the coupling-in and coupling-out elements being positioned such that the beam diverges from a focal point that is located in an optical path between the coupling-in and coupling-out elements, and at a distance that is within 3 mm of the coupling-out element.

2. The apparatus according to claim 1, wherein the power source comprises a laser.

3. The apparatus according to claim 1, wherein the coupling-in and coupling-out elements are positioned so as to create a defocused spot of light on a retina of the subject.

4. The apparatus according to claim 1, wherein a surface of the light-guiding element is shaped to form the optical coupling-in element.

5. The apparatus according to claim 1, wherein a surface of the light-guiding element is shaped to form the optical coupling-out element.

6. The apparatus according to claim 1, wherein the coupling-in and coupling-out elements are positioned such that the beam diverges at a divergence angle of 5-30 degrees.

7. The apparatus according to claim 1, wherein the extraocular device does not comprise a camera.

8. The apparatus according to claim 1, wherein the extraocular device is not configured to project an image composed of pixels.

9. The apparatus according to claim 1, wherein the extraocular device is configured to allow ambient light to enter the eye.

10. The apparatus according to claim 1, wherein the light-guiding element comprises a prism.

11. The apparatus according to claim 1, wherein the optical coupling-in element is selected from the group consisting of: a lens, a mirror, a grating, and a prism.

12. The apparatus according to claim 1, wherein the coupling-out element comprises a dichroic mirror.

* * * * *